(12) United States Patent
Hall et al.

(10) Patent No.: US 11,911,585 B2
(45) Date of Patent: Feb. 27, 2024

(54) METHODS AND SYSTEMS FOR COUPLING CONDUITS

(71) Applicant: Merit Medical Systems, Inc., South Jordan, UT (US)

(72) Inventors: John Hall, North Salt Lake, UT (US); Wayne Mower, Bountiful, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 301 days.

(21) Appl. No.: 16/039,943

(22) Filed: Jul. 19, 2018

(65) Prior Publication Data
US 2019/0022368 A1  Jan. 24, 2019

Related U.S. Application Data

(60) Provisional application No. 62/535,023, filed on Jul. 20, 2017.

(51) Int. Cl.
*A61M 39/10* (2006.01)
*A61B 17/00* (2006.01)
(Continued)

(52) U.S. Cl.
CPC ............ *A61M 39/10* (2013.01); *A61B 17/00* (2013.01); *A61B 17/11* (2013.01); *A61M 1/3655* (2013.01); *A61M 39/0247* (2013.01); *A61M 39/04* (2013.01); *A61M 39/12* (2013.01); *A61M 39/14* (2013.01); *A61B 2017/00477* (2013.01); *A61B 2017/00685* (2013.01);
(Continued)

(58) Field of Classification Search
CPC .. A61M 39/10; A61M 39/0247; A61M 39/04; A61M 39/12; A61M 39/14
See application file for complete search history.

(56) References Cited

U.S. PATENT DOCUMENTS 3,357,432 A   12/1967 Sparks
3,435,823 A   4/1969 Edwards
(Continued)

FOREIGN PATENT DOCUMENTS

DE   4418910    12/1995
DE   29515546   3/1997
(Continued)

OTHER PUBLICATIONS

International Search Report and Written Opinion dated Oct. 30, 2018 for PCT/US2018/042900.
(Continued)

*Primary Examiner* — Dung T Ulsh
(74) *Attorney, Agent, or Firm* — Dorsey & Whitney LLP

(57) ABSTRACT

Medical devices including vascular access kits and related methods are disclosed. In some embodiments, a vascular access system may include a first conduit, a second conduit, and a connector that is reversibly or irreversibly coupled to both the first and second conduits such that there is a continuous lumen from the first conduit and the second conduit. In some embodiments the vascular access system may include a connector where the inside geometry of the connector enhances laminar flow. The vascular access system, when implanted and assembled, may be a fully subcutaneous surgical implant.

21 Claims, 26 Drawing Sheets

(51) Int. Cl.
    *A61B 17/11*           (2006.01)
    *A61M 1/36*            (2006.01)
    *A61M 39/02*          (2006.01)
    *A61M 39/04*          (2006.01)
    *A61M 39/08*          (2006.01)
    *A61M 39/12*          (2006.01)
    *A61M 39/14*          (2006.01)

(52) U.S. Cl.
    CPC ................ *A61B 2017/1107* (2013.01); *A61B 2017/1132* (2013.01); *A61M 2039/0258* (2013.01); *A61M 2039/0273* (2013.01); *A61M 2039/087* (2013.01)

(56) References Cited

U.S. PATENT DOCUMENTS

| | | |
|---|---|---|
| 3,490,438 A | 1/1970 | Lavender et al. |
| 3,683,926 A | 8/1972 | Suzuki |
| 3,814,137 A | 6/1974 | Martinez |
| 3,818,511 A | 6/1974 | Goldberg et al. |
| 3,826,257 A | 7/1974 | Buselmeier |
| 3,853,126 A | 12/1974 | Schulte |
| 3,882,862 A | 5/1975 | Berend |
| 3,998,222 A | 12/1976 | Shihata |
| 4,076,023 A | 2/1978 | Martinez |
| 4,133,312 A | 1/1979 | Burd |
| 4,184,489 A | 1/1980 | Burd |
| 4,214,586 A | 7/1980 | Mericle |
| 4,318,401 A | 3/1982 | Zimmernan |
| 4,366,819 A | 1/1983 | Kaster |
| 4,427,219 A | 1/1984 | Madej |
| 4,441,215 A | 4/1984 | Kaster |
| 4,447,237 A | 5/1984 | Frisch et al. |
| 4,496,349 A | 1/1985 | Cosentino |
| 4,496,350 A | 1/1985 | Cosentino |
| 4,503,568 A | 3/1985 | Madras |
| 4,550,447 A | 11/1985 | Seiler, Jr. |
| 4,619,641 A | 10/1986 | Schanzer |
| 4,655,771 A | 4/1987 | Wallersten |
| 4,723,948 A | 2/1988 | Clark et al. |
| 4,734,094 A | 3/1988 | Jacob et al. |
| 4,753,236 A | 6/1988 | Healy |
| 4,771,777 A | 9/1988 | Horzewski et al. |
| 4,772,268 A | 9/1988 | Bates |
| 4,786,345 A | 11/1988 | Wood |
| 4,790,826 A | 12/1988 | Elftman |
| 4,822,341 A | 4/1989 | Colone |
| 4,848,343 A | 7/1989 | Wallsten et al. |
| 4,850,999 A | 7/1989 | Planck |
| 4,877,661 A | 10/1989 | House et al. |
| 4,898,591 A | 2/1990 | Jang et al. |
| 4,898,669 A | 2/1990 | Tesio |
| 4,917,087 A | 4/1990 | Walsh et al. |
| 4,919,127 A | 4/1990 | Pell |
| 4,929,236 A | 5/1990 | Sampson |
| 4,955,899 A | 9/1990 | Della Corna et al. |
| 5,026,513 A | 6/1991 | House et al. |
| 5,041,098 A | 8/1991 | Loiterman et al. |
| 5,042,161 A | 8/1991 | Hodge |
| 5,053,023 A | 10/1991 | Martin |
| 5,061,275 A | 10/1991 | Wallsten et al. |
| 5,061,276 A | 10/1991 | Tu et al. |
| 5,064,435 A | 11/1991 | Porter |
| 5,084,065 A | 1/1992 | Weldon et al. |
| 5,104,402 A | 4/1992 | Melbin |
| 5,171,227 A | 12/1992 | Twardowski et al. |
| 5,171,305 A | 12/1992 | Schickling et al. |
| 5,192,289 A | 3/1993 | Jessen |
| 5,192,310 A | 3/1993 | Herweck et al. |
| 5,197,976 A | 3/1993 | Herweck et al. |
| 5,282,860 A | 2/1994 | Matsuno et al. |
| 5,330,500 A | 7/1994 | Song |
| 5,336,616 A | 8/1994 | Livesey et al. |
| 5,399,168 A | 3/1995 | Wadsworth |
| 5,405,320 A | 4/1995 | Twardowski et al. |
| 5,405,339 A | 4/1995 | Kohnen et al. |
| 5,454,790 A | 10/1995 | Dubrul |
| 5,474,268 A | 12/1995 | Yu |
| 5,474,563 A | 12/1995 | Myler et al. |
| 5,476,451 A | 12/1995 | Ensminger et al. |
| 5,496,294 A | 3/1996 | Hergenrother et al. |
| 5,509,897 A | 4/1996 | Twardowski et al. |
| 5,549,663 A | 8/1996 | Cottone, Jr. |
| 5,558,641 A | 9/1996 | Glantz et al. |
| 5,562,617 A | 10/1996 | Finch, Jr. et al. |
| 5,562,618 A | 10/1996 | Cai et al. |
| 5,591,226 A | 1/1997 | Trerotola et al. |
| 5,607,463 A | 3/1997 | Schwartz et al. |
| 5,624,413 A | 4/1997 | Markel et al. |
| 5,637,088 A | 6/1997 | Wenner et al. |
| 5,637,102 A | 6/1997 | Tolkoff et al. |
| 5,645,532 A | 7/1997 | Horgan |
| 5,647,855 A | 7/1997 | Trooskin |
| 5,669,637 A | 9/1997 | Chitty et al. |
| 5,669,881 A | 9/1997 | Dunshee |
| 5,674,272 A | 10/1997 | Bush et al. |
| 5,676,346 A | 10/1997 | Leinsing |
| 5,743,894 A | 4/1998 | Swisher |
| 5,755,773 A | 5/1998 | Schuster |
| 5,755,775 A | 5/1998 | Trerotola et al. |
| 5,792,104 A | 8/1998 | Speckman et al. |
| 5,797,879 A | 8/1998 | Decampli |
| 5,800,512 A | 9/1998 | Lentz et al. |
| 5,800,514 A | 9/1998 | Nunez et al. |
| 5,800,522 A | 9/1998 | Campbell |
| 5,810,870 A | 9/1998 | Myers et al. |
| 5,814,098 A | 9/1998 | Hinnenkamp et al. |
| 5,830,224 A | 11/1998 | Cohn et al. |
| 5,840,240 A | 11/1998 | Stenoien et al. |
| 5,866,217 A | 2/1999 | Stenoien et al. |
| 5,904,967 A | 5/1999 | Ezaki et al. |
| 5,931,829 A | 8/1999 | Burbank et al. |
| 5,931,865 A | 8/1999 | Silverman et al. |
| 5,957,974 A | 9/1999 | Thompson et al. |
| 5,997,562 A | 12/1999 | Zadno-Azizi |
| 6,001,125 A | 12/1999 | Golds et al. |
| 6,019,788 A | 2/2000 | Butters et al. |
| 6,036,724 A | 3/2000 | Lentz et al. |
| 6,102,884 A | 8/2000 | Squitieri |
| 6,156,016 A | 12/2000 | Maginot |
| 6,167,765 B1 | 1/2001 | Weitzel |
| 6,171,295 B1 | 1/2001 | Garabedian |
| 6,231,085 B1 | 5/2001 | Olson |
| 6,245,098 B1 | 6/2001 | Feeser |
| 6,255,396 B1 | 7/2001 | Ding et al. |
| 6,261,255 B1 | 7/2001 | Mullis et al. |
| 6,261,257 B1 | 7/2001 | Uflacker et al. |
| 6,280,466 B1 | 8/2001 | Kugler et al. |
| 6,308,992 B1 | 10/2001 | Mitsui et al. |
| 6,309,411 B1 | 10/2001 | Lashinski et al. |
| 6,319,279 B1 | 11/2001 | Shannon et al. |
| 6,338,724 B1 | 1/2002 | Dossa |
| 6,398,764 B1 | 6/2002 | Finch, Jr. et al. |
| 6,402,767 B1 | 6/2002 | Nash et al. |
| 6,428,571 B1 | 8/2002 | Lentz et al. |
| 6,436,132 B1 | 8/2002 | Patel et al. |
| 6,582,409 B1 | 6/2003 | Squitieri |
| 6,585,762 B1 | 7/2003 | Stanish |
| 6,610,004 B2 | 8/2003 | Viole et al. |
| 6,689,096 B1 | 2/2004 | Loubens et al. |
| 6,689,157 B2 | 2/2004 | Madrid et al. |
| 6,692,461 B2 | 2/2004 | Wantink |
| 6,699,233 B2 | 3/2004 | Slanda et al. |
| 6,702,748 B1 | 3/2004 | Nita et al. |
| 6,702,781 B1 | 3/2004 | Reifart et al. |
| 6,706,025 B2 | 3/2004 | Engelson et al. |
| 6,719,781 B1 | 4/2004 | Kim |
| 6,719,783 B2 | 4/2004 | Lentz et al. |
| 6,730,096 B2 | 5/2004 | Basta |
| 6,733,459 B1 | 5/2004 | Atsumi |
| 6,740,273 B2 | 5/2004 | Lee |
| 6,749,574 B2 | 6/2004 | O'Keefe |
| 6,752,826 B2 | 6/2004 | Holloway et al. |

(56) References Cited

U.S. PATENT DOCUMENTS

| | | |
|---|---|---|
| 6,758,836 B2 | 7/2004 | Zawacki |
| 6,858,019 B2 | 2/2005 | McGuckin, Jr. et al. |
| 6,926,724 B1 | 8/2005 | Chu |
| 6,926,735 B2 | 8/2005 | Henderson |
| 6,976,952 B1 | 12/2005 | Maini et al. |
| 6,981,987 B2 | 1/2006 | Huxel et al. |
| 7,011,645 B2 | 3/2006 | McGuckin, Jr. et al. |
| 7,025,741 B2 | 4/2006 | Cull |
| 7,036,599 B2 | 5/2006 | Matteucci |
| 7,044,937 B1 | 5/2006 | Kirwan et al. |
| 7,101,356 B2 | 9/2006 | Miller |
| 7,131,959 B2 | 11/2006 | Blatter |
| 7,211,074 B2 | 5/2007 | Sansoucy |
| 7,244,271 B2 | 7/2007 | Lenz et al. |
| 7,244,272 B2 | 7/2007 | Dubson et al. |
| 7,252,649 B2 | 8/2007 | Sherry |
| 7,297,158 B2 | 11/2007 | Jensen |
| 7,351,257 B2 | 4/2008 | Kaldany |
| 7,399,296 B2 | 7/2008 | Poole et al. |
| 7,438,699 B2 | 10/2008 | Pecor et al. |
| 7,452,374 B2 | 11/2008 | Hain et al. |
| 7,507,229 B2 | 3/2009 | Hewitt et al. |
| 7,588,551 B2 | 9/2009 | Gertner |
| 7,607,237 B2 | 10/2009 | Schafer |
| 7,708,722 B2 | 5/2010 | Glenn |
| 7,722,665 B2 | 5/2010 | Anwar et al. |
| RE41,448 E | 7/2010 | Squitieri |
| 7,762,977 B2 | 7/2010 | Porter et al. |
| 7,789,908 B2 | 9/2010 | Sowinski et al. |
| 7,828,833 B2 | 11/2010 | Haverkost et al. |
| 7,833,214 B2 | 11/2010 | Wilson et al. |
| 7,846,139 B2 | 12/2010 | Zinn et al. |
| 7,850,675 B2 | 12/2010 | Bell et al. |
| 7,850,705 B2 | 12/2010 | Bachinski et al. |
| 7,922,757 B2 | 4/2011 | McGuckin |
| D637,500 S | 5/2011 | Corbin |
| 7,972,314 B2 | 7/2011 | Bizup et al. |
| 8,079,973 B2 | 12/2011 | Herrig et al. |
| 8,092,435 B2 | 1/2012 | Beling et al. |
| 8,097,311 B2 | 1/2012 | Wang et al. |
| 8,313,524 B2 | 11/2012 | Edwin et al. |
| 8,388,634 B2 | 3/2013 | Rubenstein et al. |
| 8,512,312 B2 * | 8/2013 | Sage ................. A61M 39/1011 604/535 |
| 8,551,139 B2 | 10/2013 | Surti et al. |
| 8,690,815 B2 | 4/2014 | Porter et al. |
| 8,951,355 B2 | 2/2015 | Boyle, Jr. et al. |
| 9,278,172 B2 | 3/2016 | Herrig et al. |
| 9,642,623 B2 * | 5/2017 | Agarwal ................. A61B 17/11 |
| 9,731,113 B2 | 8/2017 | Grace et al. |
| 10,172,673 B2 | 1/2019 | Viswanathan et al. |
| 2001/0011421 A1 | 8/2001 | Bakke et al. |
| 2001/0053930 A1 | 12/2001 | Kugler et al. |
| 2002/0049403 A1 | 4/2002 | Alanis |
| 2002/0055766 A1 | 5/2002 | Wallace et al. |
| 2002/0055771 A1 | 5/2002 | Sandock |
| 2002/0099432 A1 | 7/2002 | Yee |
| 2002/0151761 A1 | 10/2002 | Viole et al. |
| 2003/0100859 A1 | 5/2003 | Henderson et al. |
| 2003/0125789 A1 | 7/2003 | Ross et al. |
| 2003/0135258 A1 | 7/2003 | Andreas et al. |
| 2003/0135261 A1 | 7/2003 | Kugler et al. |
| 2003/0139806 A1 | 7/2003 | Haverkost et al. |
| 2003/0181969 A1 | 9/2003 | Kugler et al. |
| 2003/0212385 A1 | 11/2003 | Brenner et al. |
| 2003/0212431 A1 | 11/2003 | Brady et al. |
| 2004/0024442 A1 | 2/2004 | Sowinski et al. |
| 2004/0054405 A1 * | 3/2004 | Richard ............. A61B 17/0643 623/1.36 |
| 2004/0073282 A1 * | 4/2004 | Stanish ................. A61B 17/11 623/1.36 |
| 2004/0078071 A1 | 4/2004 | Escamilla et al. |
| 2004/0099395 A1 | 5/2004 | Wang et al. |
| 2004/0147866 A1 | 7/2004 | Blatter et al. |
| 2004/0193242 A1 | 9/2004 | Lentz et al. |
| 2004/0215058 A1 | 10/2004 | Zirps et al. |
| 2004/0215337 A1 | 10/2004 | Hain et al. |
| 2004/0236412 A1 | 11/2004 | Brar |
| 2005/0004553 A1 | 1/2005 | Douk |
| 2005/0137614 A1 * | 6/2005 | Porter ................. A61M 1/3655 606/153 |
| 2005/0192559 A1 | 9/2005 | Michels et al. |
| 2005/0203457 A1 | 9/2005 | Smego |
| 2005/0209581 A1 | 9/2005 | Butts et al. |
| 2005/0215938 A1 | 9/2005 | Khan et al. |
| 2006/0004392 A1 | 1/2006 | Amarant |
| 2006/0029465 A1 | 2/2006 | Auer |
| 2006/0058867 A1 | 3/2006 | Thistle et al. |
| 2006/0064159 A1 | 3/2006 | Porter et al. |
| 2006/0081260 A1 | 4/2006 | Eells et al. |
| 2006/0118236 A1 | 6/2006 | House et al. |
| 2007/0038288 A1 | 2/2007 | Lye et al. |
| 2007/0078412 A1 | 4/2007 | McGuckin, Jr. et al. |
| 2007/0078416 A1 | 4/2007 | Eliasen |
| 2007/0078438 A1 | 4/2007 | Okada |
| 2007/0088336 A1 | 4/2007 | Dalton |
| 2007/0123811 A1 | 5/2007 | Squitieri |
| 2007/0135775 A1 | 6/2007 | Edoga et al. |
| 2007/0142850 A1 | 6/2007 | Fowler |
| 2007/0161958 A1 | 7/2007 | Glenn |
| 2007/0167901 A1 | 7/2007 | Herrig et al. |
| 2007/0168019 A1 | 7/2007 | Amplatz et al. |
| 2007/0173868 A1 | 7/2007 | Bachinski et al. |
| 2007/0191779 A1 | 8/2007 | Shubayev et al. |
| 2007/0197856 A1 | 8/2007 | Gellman et al. |
| 2007/0213838 A1 | 9/2007 | Hengelmolen |
| 2007/0219510 A1 | 9/2007 | Zinn et al. |
| 2007/0233018 A1 | 10/2007 | Bizup et al. |
| 2007/0244539 A1 | 10/2007 | Lentz et al. |
| 2007/0249986 A1 | 10/2007 | Smego |
| 2007/0249987 A1 | 10/2007 | Gertner |
| 2007/0265584 A1 | 11/2007 | Hickman et al. |
| 2007/0293823 A1 | 12/2007 | Sherry |
| 2007/0293829 A1 | 12/2007 | Conlon et al. |
| 2008/0009781 A1 | 1/2008 | Anwar et al. |
| 2008/0027534 A1 | 1/2008 | Edwin et al. |
| 2008/0132924 A1 | 6/2008 | McGuckin |
| 2008/0167595 A1 | 7/2008 | Porter et al. |
| 2008/0221469 A1 * | 9/2008 | Shevchuk ........ A61M 16/0816 600/532 |
| 2008/0306580 A1 | 12/2008 | Jenson et al. |
| 2009/0076587 A1 * | 3/2009 | Cully ....................... A61F 2/064 623/1.42 |
| 2009/0137944 A1 | 5/2009 | Haarala et al. |
| 2009/0179422 A1 | 7/2009 | Werth |
| 2009/0187158 A1 | 7/2009 | Richmond |
| 2009/0227932 A1 | 9/2009 | Herrig |
| 2009/0234267 A1 | 9/2009 | Ross |
| 2009/0318895 A1 | 12/2009 | Lachner |
| 2010/0154800 A1 | 6/2010 | Chang et al. |
| 2010/0160718 A1 | 6/2010 | Villafana et al. |
| 2010/0160847 A1 | 6/2010 | Braido et al. |
| 2010/0161040 A1 | 6/2010 | Braido et al. |
| 2010/0198079 A1 | 8/2010 | Ross |
| 2010/0268188 A1 | 10/2010 | Hanson |
| 2010/0268196 A1 | 10/2010 | Hastings et al. |
| 2010/0292774 A1 | 11/2010 | Shalev |
| 2011/0011421 A1 | 1/2011 | Dumas et al. |
| 2011/0015723 A1 | 1/2011 | Batiste et al. |
| 2011/0054312 A1 | 3/2011 | Bell et al. |
| 2011/0060264 A1 | 3/2011 | Porter et al. |
| 2011/0112482 A1 | 5/2011 | Redd |
| 2011/0208218 A1 | 8/2011 | Ball |
| 2011/0257609 A1 | 10/2011 | Bizup et al. |
| 2011/0264080 A1 | 10/2011 | Lim et al. |
| 2011/0295181 A1 | 12/2011 | Dann et al. |
| 2012/0059305 A1 | 3/2012 | Akingba |
| 2012/0065652 A1 | 3/2012 | Cully et al. |
| 2012/0078202 A1 | 3/2012 | Beling et al. |
| 2013/0060268 A1 * | 3/2013 | Herrig ................. A61M 60/37 606/153 |
| 2013/0204275 A1 | 8/2013 | Agarwal et al. |
| 2013/0338559 A1 | 12/2013 | Franano et al. |
| 2014/0018721 A1 | 1/2014 | Gage et al. |

(56) References Cited

U.S. PATENT DOCUMENTS

| | | | |
|---|---|---|---|
| 2014/0094841 A1 | 4/2014 | Sutton et al. | |
| 2014/0155908 A1 | 6/2014 | Rosenbluth et al. | |
| 2014/0276215 A1 | 9/2014 | Nelson | |
| 2014/0288638 A1 | 9/2014 | Knight et al. | |
| 2014/0371779 A1 | 12/2014 | Vale et al. | |
| 2015/0051532 A1 | 2/2015 | Tomko et al. | |
| 2015/0082604 A1 | 3/2015 | Cully et al. | |
| 2015/0094744 A1* | 4/2015 | Aghayev | A61B 17/12045 606/153 |
| 2015/0150640 A1 | 6/2015 | Boyle et al. | |
| 2015/0257775 A1 | 9/2015 | Gilvarry et al. | |
| 2015/0265393 A1 | 9/2015 | Stonebridge et al. | |
| 2016/0030708 A1* | 2/2016 | Casiello | A61M 25/0023 604/218 |
| 2016/0066954 A1 | 3/2016 | Miller et al. | |
| 2016/0129177 A1 | 5/2016 | Herrig | |
| 2016/0136398 A1 | 6/2016 | Heilman et al. | |
| 2016/0279317 A1 | 9/2016 | Gale et al. | |
| 2017/0020556 A1 | 1/2017 | Sutton et al. | |
| 2018/0271637 A1 | 9/2018 | Hall et al. | |
| 2019/0015627 A1 | 1/2019 | Hall et al. | |
| 2019/0022368 A1 | 1/2019 | Hall et al. | |
| 2019/0126017 A1 | 5/2019 | Hall et al. | |

FOREIGN PATENT DOCUMENTS

| | | |
|---|---|---|
| DE | 102008055587 | 8/2009 |
| EP | 0540834 | 5/1993 |
| EP | 1797831 | 6/2007 |
| JP | 5714358 | 1/1982 |
| JP | 62112567 | 5/1987 |
| JP | 04507050 | 12/1992 |
| JP | 05212107 | 8/1993 |
| JP | 06105798 | 4/1994 |
| JP | 0984871 | 3/1997 |
| JP | 09264468 | 7/1997 |
| JP | 2003501223 | 1/2003 |
| JP | 3995057 | 10/2007 |
| JP | 2008511414 | 4/2008 |
| KR | 101026933 | 4/2011 |
| KR | 1020110036848 | 4/2011 |
| WO | 198403036 | 8/1984 |
| WO | 1990085509 | 8/1990 |
| WO | 199519200 | 7/1995 |
| WO | 199624399 | 8/1996 |
| WO | 1998034676 | 8/1998 |
| WO | 2000027299 | 5/2000 |
| WO | 200076577 | 12/2000 |
| WO | 200105447 | 1/2001 |
| WO | 200105463 | 1/2001 |
| WO | 2001005463 | 1/2001 |
| WO | 2001028456 | 4/2001 |
| WO | 2004032991 | 4/2004 |
| WO | 2004112880 | 12/2004 |
| WO | 2006026687 | 9/2006 |
| WO | 2009059371 | 5/2009 |
| WO | 2010059102 | 5/2010 |
| WO | 2011060386 | 5/2011 |
| WO | 2011153302 | 12/2011 |
| WO | 2015023460 | 2/2015 |
| WO | 2015100251 | 7/2015 |

OTHER PUBLICATIONS

European Search Report dated Jun. 8, 2005 for EP05006233.0.
European Search Report dated Dec. 3, 2013 for EP05793066.1.
International Preliminary Report dated Mar. 12, 2014 for PCT/US2012/053967.
International Search Report and Written Opinion dated Jan. 28, 2015 for PCT/US2014/049547.
International Search Report and Written Opinion dated Mar. 15, 2013 for PCT/US2012/053967.
International Search Report and Written Opinion dated Mar. 16, 2015 for PCT/US2014/046630.
International Search Report and Written Opinion dated May 2, 2018 for PCT/US2018/013326.
International Search Report and Written Opinion dated May 3, 2013 for PCT/US2012/053967.
International Search Report and Written Opinion dated May 6, 1998 for PCT/US1998/001939.
International Search Report and Written Opinion dated Jun. 3, 2009 for PCT/US2009/035923.
International Search Report and Written Opinion dated Jun. 20, 2007 for PCT/US2006/044564.
International Search Report and Written Opinion dated Jun. 22, 2018 for PCT/US2018/014371.
Notice of Allowance dated Mar. 15, 2010 for U.S. Appl. No. 11/216,536.
Notice of Allowance dated Oct. 4, 2013 for U.S. Appl. No. 12/831,092.
Office Action dated Jan. 9, 2018 for U.S. Appl. No. 14/450,468.
Office Action dated Feb. 6, 2013 for U.S. Appl. No. 12/831,092.
Office Action dated Feb. 21, 2017 for U.S. Appl. No. 14/192,567.
Office Action dated Mar. 15, 2018 for U.S. Appl. No. 14/332,091.
Office Action dated May 5, 2010 for U.S. Appl. No. 10/962,200.
Office Action dated May 24, 2018 for U.S. Appl. No. 14/995,270.
Office Action dated Jun. 4, 2018 for U.S. Appl. No. 14/192,567.
Office Action dated Jun. 9, 2016 for U.S. Appl. No. 14/192,567.
Office Action dateed Jun. 15, 2017 for U.S. Appl. No. 14/192,567.
Office Action dated Jul. 11, 2018 for U.S. Appl. No. 14/450,468.
Office Action dated Aug. 7, 2017 for U.S. Appl. No. 14/450,468.
Office Action dated Aug. 12, 2010 for U.S. Appl. No. 10/962,200.
Office Action dated Aug. 15, 2016 for U.S. Appl. No. 14/332,091.
Office Action dated Sep. 20, 2012 for U.S. Appl. No. 12/831,092.
Office Action dated Oct. 27, 2015 for U.S. Appl. No. 14/192,567.
Office Action dated Nov. 26, 2007 for U.S. Appl. No. 10/962,200.
Office Action dated Dec. 5, 2017 for U.S. Appl. No. 14/995,270.
Office Action dated Dec. 20, 2017 for U.S. Appl. No. 14/192,567.
Office Action dated Dec. 30, 2016 for U.S. Appl. No. 14/450,468.
Clinical Reveiw of MTI, Onxy Liquid Embolization System, available at http://www.fda.gov/ohrms/dockets/ac/03/briefing/3975b1-02-clinical-review.pdf. accessed Aug. 29, 2005.
Besarab, et al., Measuring the Adequacy of Hemodialysis Access, Current Opinion in Nephrology and Hypertension, Rapid Science Publishers ISSN , 1996 , 1062-4821.
Coulson MD, et al., Modification of Venous End of Dialysis Grafts: An Attempt to Reduce Neointimal Hyperplasia, Dialysis & Transplantation, vol. 29 No. 1 ,Jan. 2000 , 10-18.
Coulson MD, PhD, et al., A Combination of the Elephant Trunk Anastomosis Technique and Vascular Clips for Dialysis Grafts, Surgical Rounds ,Nov. 1999 ,596-608.
Kanterman, et al., Dialysis Access Grafts: Anatomic Location of Venous Stenosis and Results of Angioplasty, Interventional Radiology, vol. 195 No. 1, 195 ,Apr. 1995 , 135-139.
Kumpe, et al., Angioplasty/Thrombolytic Treatment of Failing and Failed Hemodialysis Access Sites: Comparison with Surgical Treatment, Progress in Cardiovascular Diseases, vol. XXXIV No. 4 , Jan./Feb. 1992 ,263-278.
Lin, et al., Contemporary Vascular Access Surgery for Chronic Haemodialysis, They Royal College of Surgeons of Edinburgh, J.R. Coll, Surg, Edinb., 41 ,Jun. 1996 , 164-169.
Peterson, et al., Subclavian Venous Stenosis: A Complication of Subclavian Dialysis, The Journal of American Medical Association, vol. 252 No. 24 , Dec. 28, 1994 ,3404-3406.
Raju M.D., et al., Techniques for Insertion and Management of Complications, PTFE Grafts for Hemodialysis Access, Ann. Surg., vol. 206 No. 5 ,Nov. 1987 ,666-673.
Sharafuddin, et al., Percutaneous Balloon-Assisted Aspiration Thrombectomy of clotted ahemodialysis Access Grafts, Journal of Vascular and Interventional Radiology, vol. 7 No. 2 ,Mar.-Apr. 1996 , 177-183.
Office Action dated Apr. 16, 2020 for U.S. Appl. No. 15/868,313.
European Search Report dated Mar. 10, 2021 for EP18835705.7.
Office Action dated Oct. 1, 2020 for U.S. Appl. No. 15/868,313.
Office Action dated Apr. 27, 2021 for U.S. Appl. No. 15/868,313.
Office Action dated Nov. 19, 2021 for U.S. Appl. No. 15/868,313.

(56) References Cited

OTHER PUBLICATIONS

European Search Report dated Mar. 22, 2021 for EP18832124.4.
European Search Report dated Jul. 24, 2020 for EP18738538.0.
European Search Report dated Oct. 2, 2020 for EP18745239.6.
European Search Report dated Oct. 26, 2020 for EP18738538.0.
European Search Report dated Oct. 28, 2020 for EP18771028.0.
European Search Report dated Dec. 4, 2020 for 18764826.6.
International Search Report and Written Opinion dated Jan. 18, 2019 for PCT/US2018/041821.
International Search Report and Written Opinion dated Apr. 4, 2019 for PCT/US2018/058179.
International Search Report and Written Opinion dated Jun. 15, 2018 for PCT/US2018/020614.
International Search Report and Written Opinion dated Jul. 17, 2018 for PCT/US2018/023956.
Notice of Allowance dated Mar. 3, 2020 for U.S. Appl. No. 15/035,626.
Notice of Allowance dated Mar. 11, 2020 for U.S. Appl. No. 15/828,040.
Notice of Allowance dated Mar. 24, 2021 for U.S. Appl. No. 15/910,273.
Notice of Allowance dated Aug. 3, 2021 for U.S. Appl. No. 16/033,515.
Notice of Allowance dated Oct. 2, 2020 for U.S. Appl. No. 15/933,815.
Notice of Allowance dated Oct. 5, 2018 for U.S. Appl. No. 15/093,622.
Notice of Allowance dated Nov. 6, 2018 for U.S. Appl. No. 14/995,270.
Office Action dated Jan. 8, 2019 for U.S. Appl. No. 15/035,626.
Office Action dated Feb. 18, 2022 for U.S. Appl. No. 15/875,194.
Office Action dated Mar. 3, 2021 for U.S. Appl. No. 15/934,152.
Office Action dated Mar. 10, 2022 for U.S. Appl. No. 15/934,152.
Office Action dated Mar. 29, 2019 for U.S. Appl. No. 14/332,091.
Office Action dated Mar. 29, 2021 for U.S. Appl. No. 16/033,515.
Office Action dated Apr. 6, 2021 for U.S. Appl. No. 16/284,526.
Office Action dated Apr. 17, 2020 for U.S. Appl. No. 15/875,194.
Office Action dated Apr. 17, 2020 for U.S. Appl. No. 15/934,152.
Office Action dated Apr. 21, 2021 for U.S. Appl. No. 15/875,194.
Office Action dated Apr. 28, 2020 for U.S. Appl. No. 14/192,567.
Office Action dated May 1, 2020 for U.S. Appl. No. 15/693,010.
Office Action dated May 5, 2020 for U.S. Appl. No. 15/910,273.
Office Action dated May 21, 2021 for U.S. Appl. No. 15/826,977.
Office Action dated May 22, 2019 for U.S. Appl. No. 14/450,468.
Office Action dated Jun. 15, 2021 for U.S. Appl. No. 15/934,152.
Office Action dated Jun. 17, 2019 for U.S. Appl. No. 15/035,626.
Office Action dated Jul. 19, 2018 for U.S. Appl. No. 15/035,626.
Office Action dated Jul. 23, 2019 for U.S. Appl. No. 14/332,091.
Office Action dated Aug. 5, 2020 for U.S. Appl. No. 15/875,194.
Office Action dated Aug. 18, 2020 for U.S. Appl. No. 15/934,152.
Office Action dated Aug. 21, 2019 for U.S. Appl. No. 14/192,567.
Office Action dated Sep. 22, 2021 for U.S. Appl. No. 15/875,194.
Office Action dated Sep. 26, 2019 for U.S. Appl. No. 15/693,010.
Office Action dated Sep. 30, 2019 for U.S. Appl. No. 15/875,194.
Office Action dated Oct. 1, 2018 for U.S. Appl. No. 14/332,091.
Office Action dated Oct. 6, 2021 for U.S. Appl. No. 15/934,152.
Office Action dated Oct. 17, 2019 for U.S. Appl. No. 15/828,040.
Office Action dated Oct. 22, 2019 for U.S. Appl. No. 15/035,526.
Office Action dated Nov. 24, 2020 for U.S. Appl. No. 15/826,977.
Office Action dated Nov. 29, 2019 for U.S. Appl. No. 15/934,152.
Office Action dated Nov. 30, 2020 for U.S. Appl. No. 15/910,273.
Office Action dated Dec. 5, 2018 for U.S. Appl. No. 14/450,468.
Office Action dated Dec. 7, 2018 for U.S. Appl. No. 14/192,567.
Office Action dated Dec. 7, 2020 for U.S. Appl. No. 16/033,515.
Notice of Allowance dated Mar. 31, 2022 for U.S. Appl. No. 15/868,313.
European Examination Report dated Aug. 25, 2023 for EP187385380.

\* cited by examiner

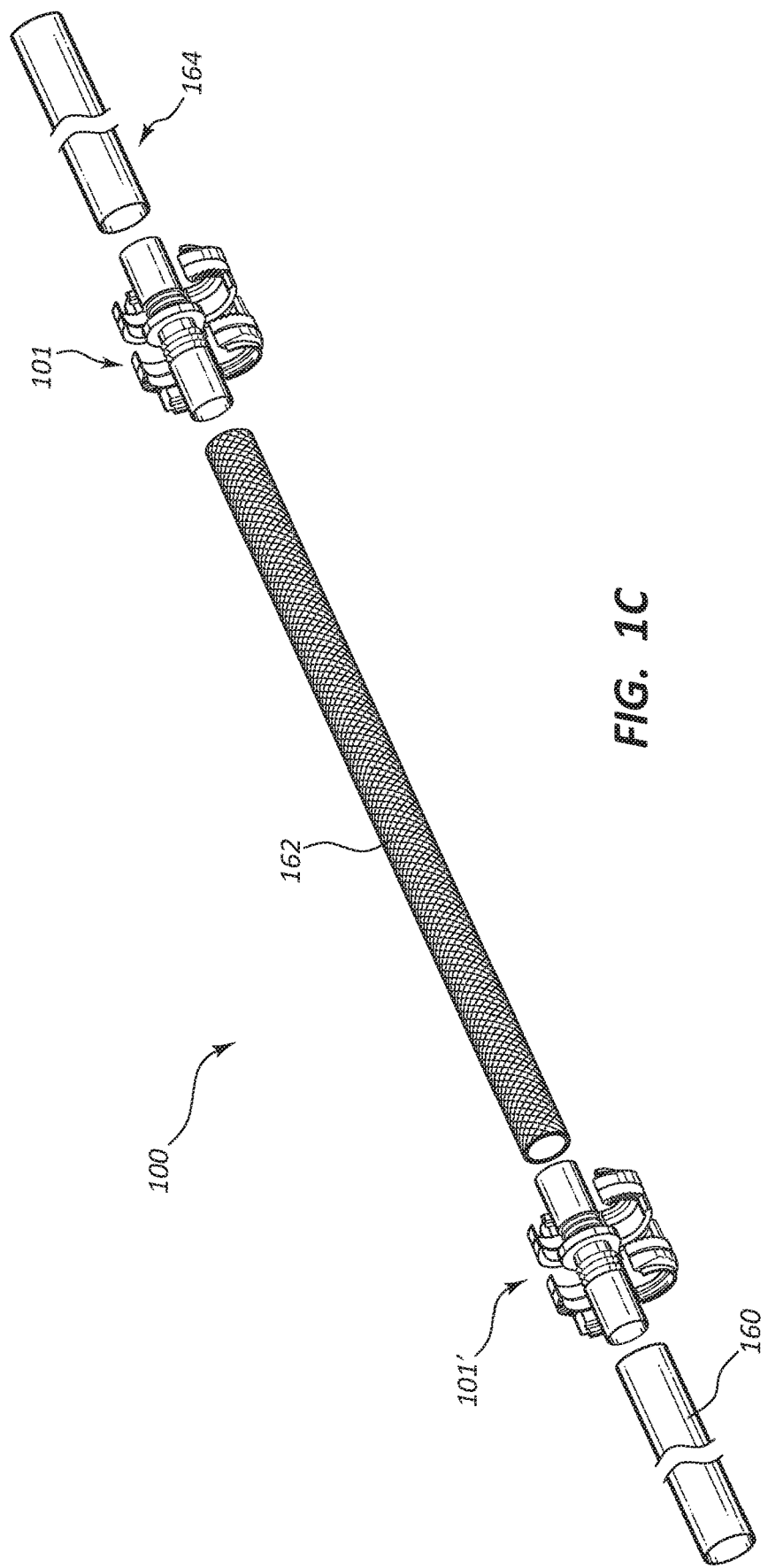

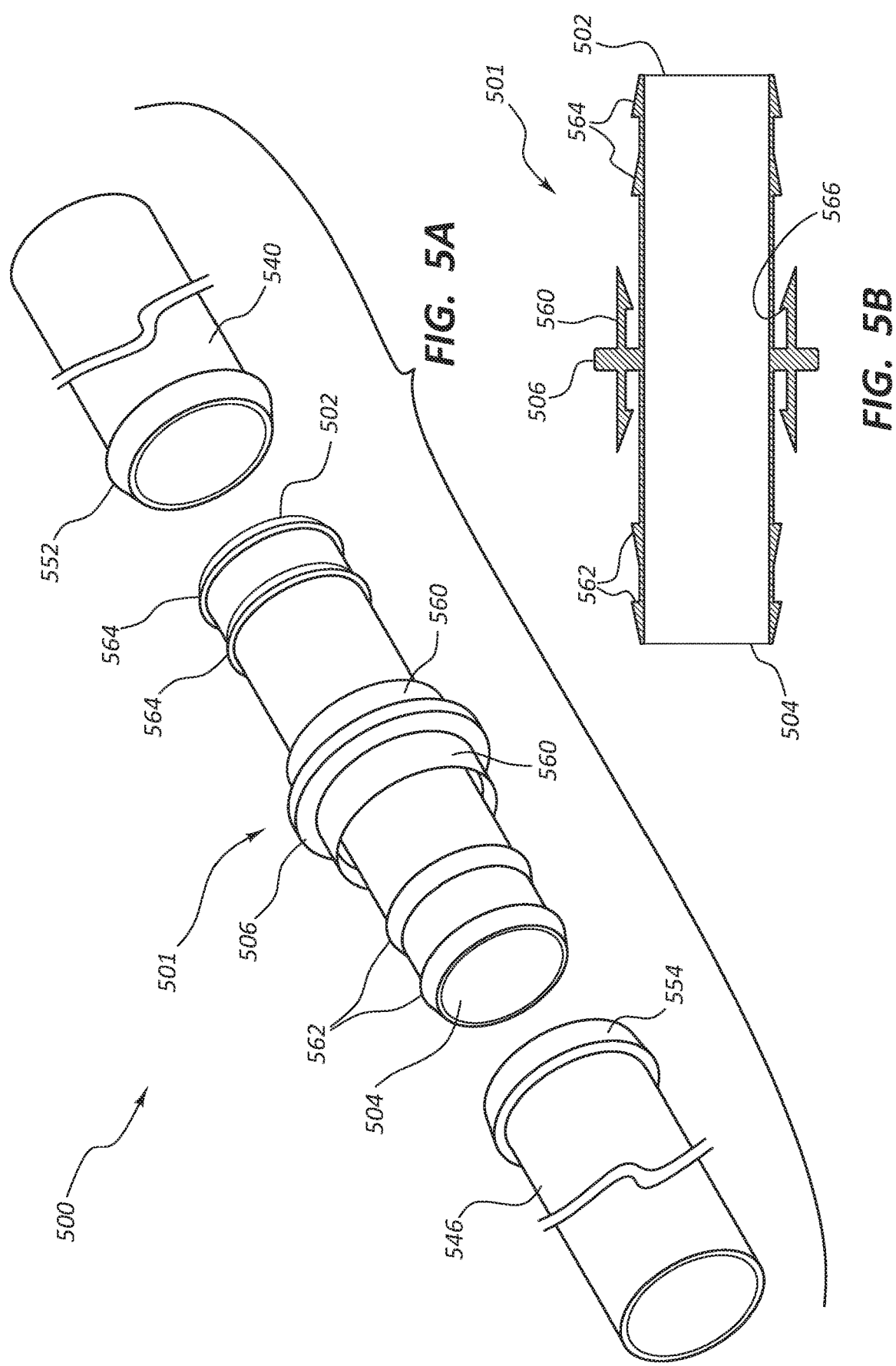

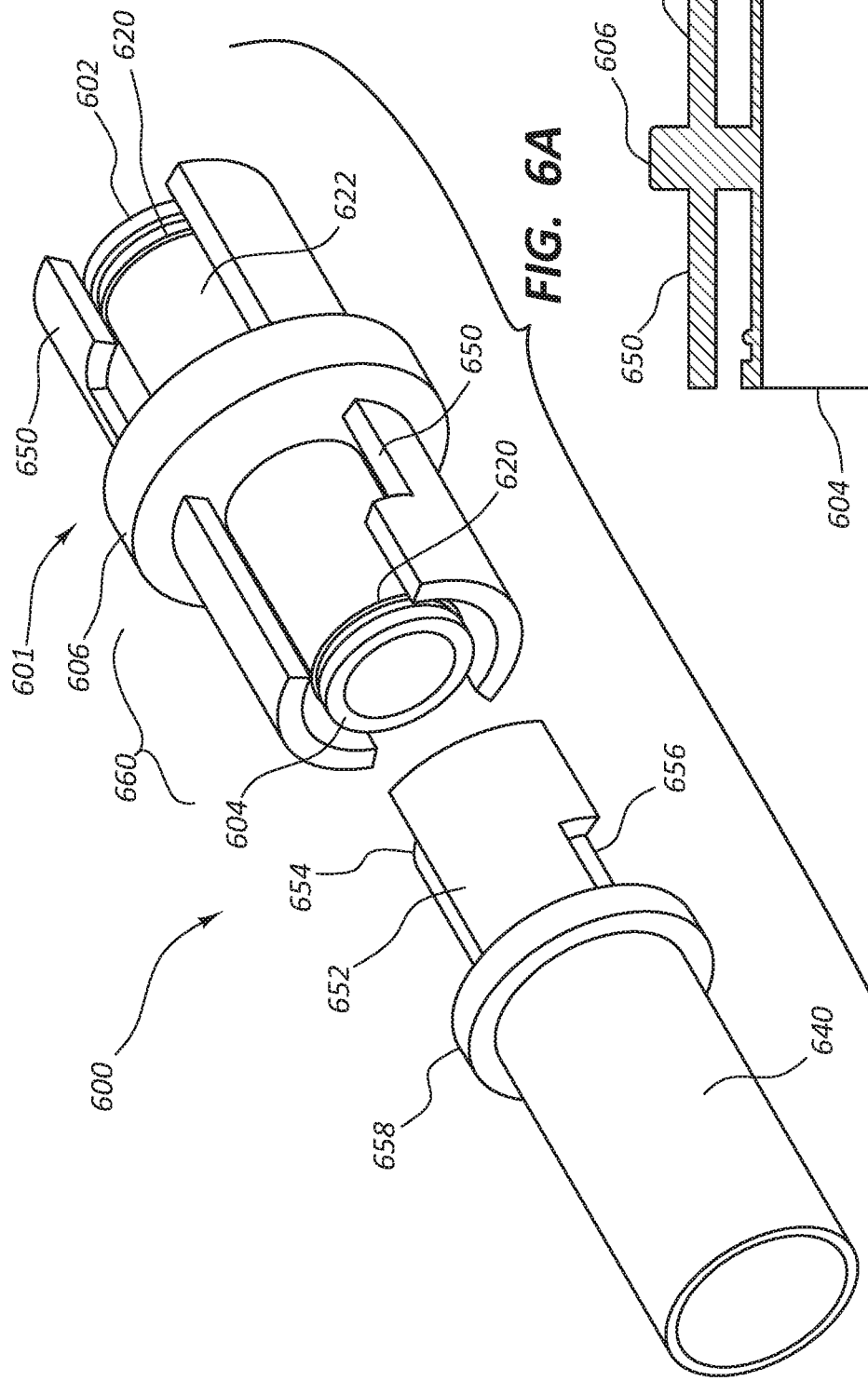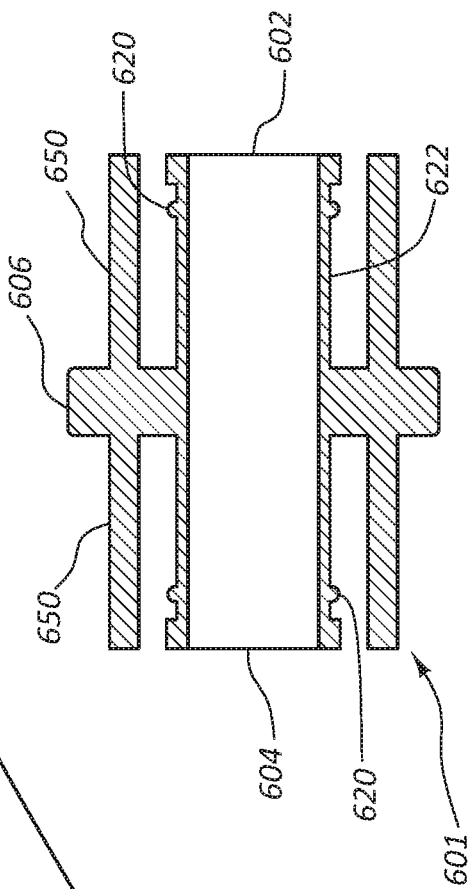
FIG. 6A
FIG. 6B

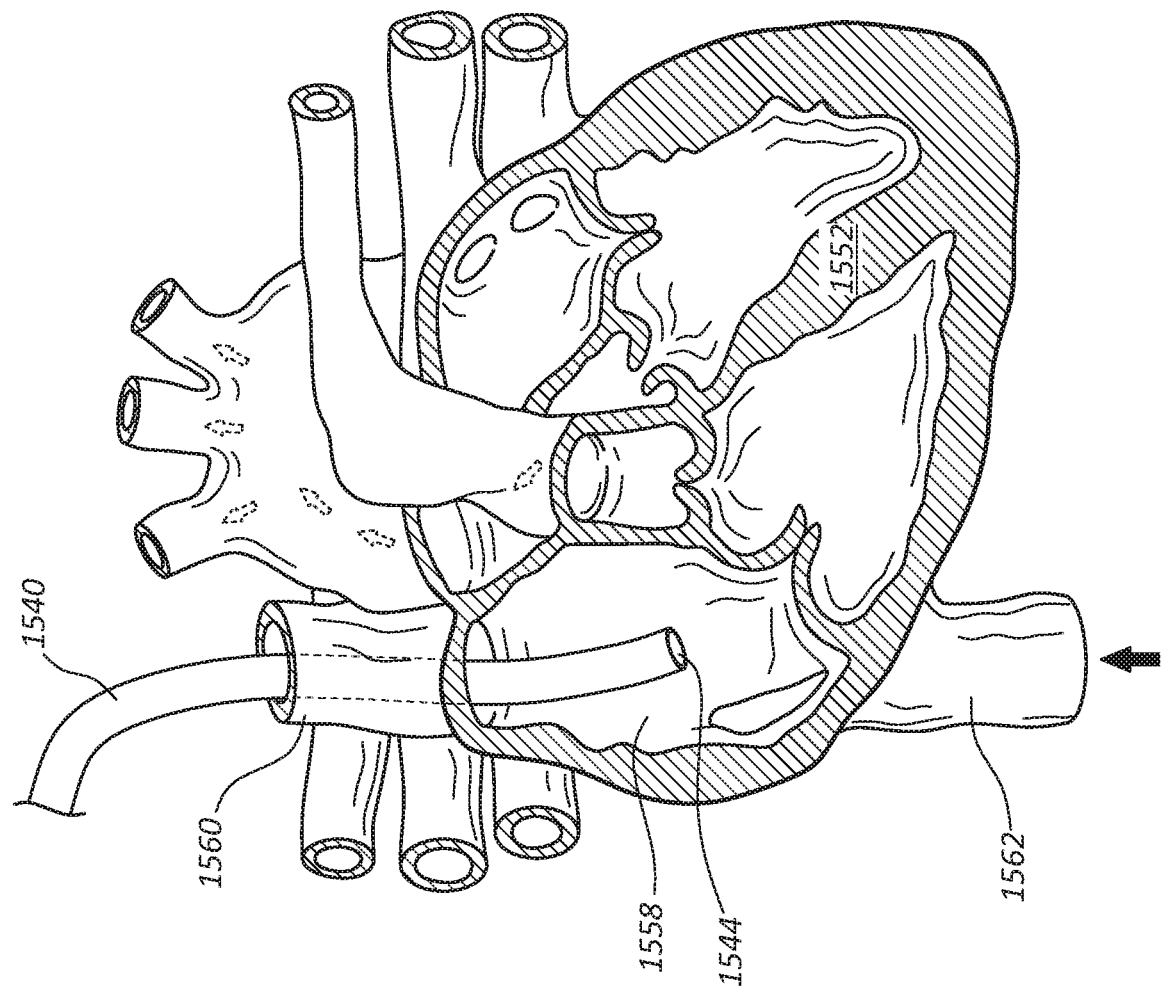

METHODS AND SYSTEMS FOR COUPLING CONDUITS

RELATED APPLICATIONS

This application claims priority to U.S. Provisional Application No. 62/535,023, filed on Jul. 20, 2017 and titled "Methods and Systems for Coupling Conduits" which is hereby incorporated by reference in its entirety.

TECHNICAL FIELD

The field of the present disclosure relates generally to medical devices. More specifically, the present disclosure relates to conduits, such as catheters and grafts, which are used to provide access into the body and methods and systems for coupling conduits. In some embodiments, the present disclosure relates to coupling one or more conduits together.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 1C is a simplified perspective view of certain components of a vascular access system including components of the system of FIG. 1A;

FIG. 5A is a simplified perspective view of certain components of a vascular access system;

FIG. 5B is a simplified cross-section view of certain components of the vascular access system of FIG. 5A;

FIG. 6A is a simplified perspective view of certain components of a vascular access system;

FIG. 6B is a simplified cross-section view of certain components of the vascular access system of FIG. 6A;

FIG. 15B is a detailed cross-section view of the heart of the patient with certain components of the vascular access system of FIG. 15A positioned inside the right atrium;

DETAILED DESCRIPTION

Figure 1A:
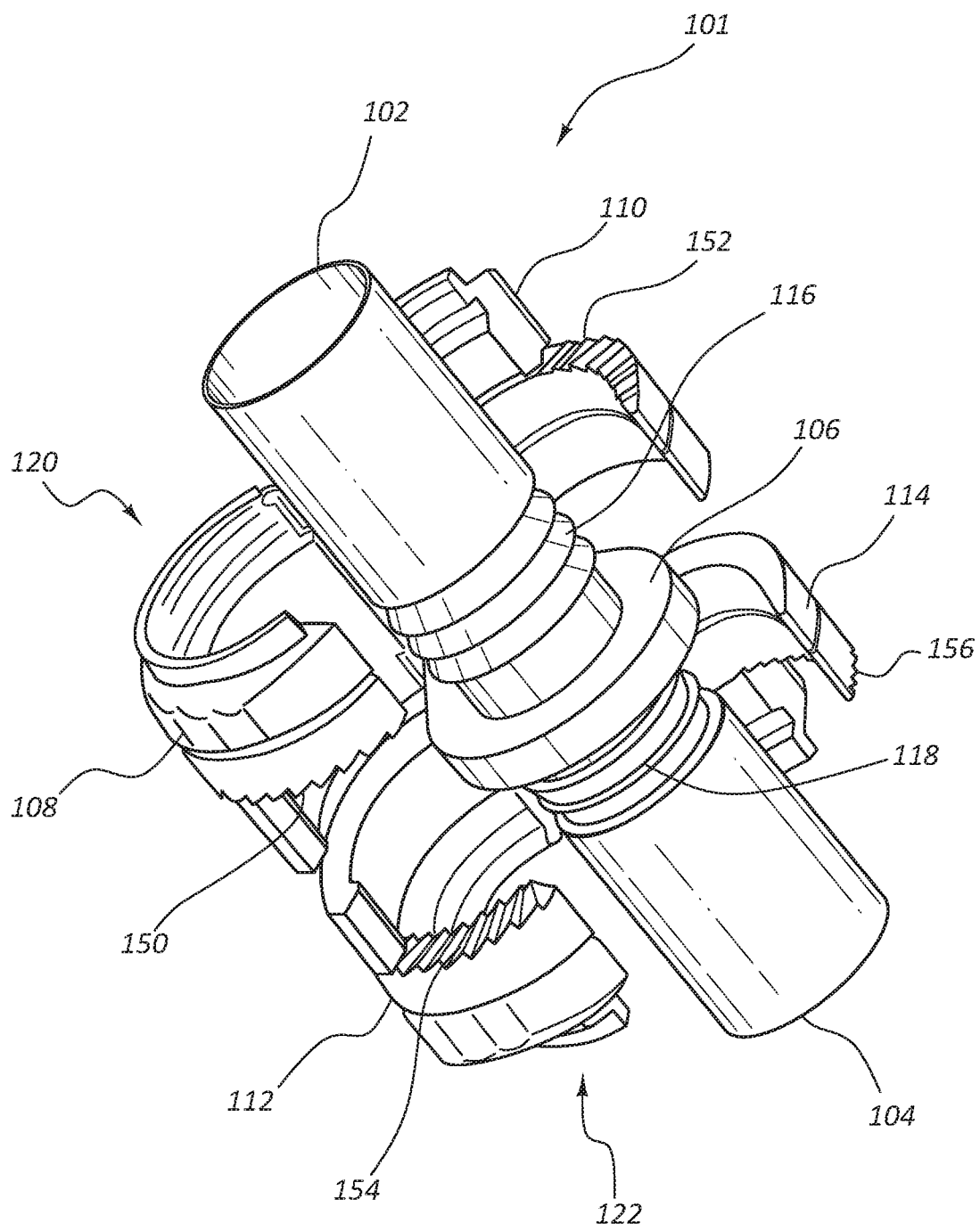
FIG. 1A is a simplified perspective view of certain components of a vascular access system.

In the United States, approximately 400,000 people have end-stage renal disease requiring chronic hemodialysis. Permanent vascular access sites for performing hemodialysis may be formed by creating an arteriovenous (AV) anastomosis whereby a vein is attached to an artery to form a high-flow shunt or fistula. A vein may be directly attached to an artery, but it may take six to eight weeks before the venous section of the fistula has sufficiently healed and matured to provide adequate blood flow for use with hemodialysis. Moreover, a direct anastomosis may not be feasible in all patients due to anatomical considerations.

Other patients may require the use of artificial graft material to provide an access site between the arterial and venous vascular systems. However, AV grafts still require time for the graft material to mature prior to use, so that a temporary access device must be inserted into a patient for hemodialysis access until the AV graft has matured. The use of temporary catheter access exposes the patient to additional risk of bleeding and infection, as well as discomfort. In addition, patency rates of grafts are still not satisfactory, as the overall graft failure rate may be high. Failure of these grafts is usually due to stenosis at the venous end. These failure rates are further increased in higher-risk patients, such as diabetics, in whom the vascular access is most needed. These access failures result in disruption in the routine dialysis schedule and create hospital costs of over $2 billion per year.

In some vascular access systems and methods it may be advantageous to use multiple conduits to improve anastomosis with the vasculature and extravascular flow properties. When using multiple conduits, such as multiple artificial vascular catheters, that are connected to each other in the body the conduits may or may not be labeled with outside diameter measurements. Conduits may be labeled according to the inside diameter of the conduit and, as wall thickness and other parameters may vary between conduits of different design or manufacture, the outside diameter may not consistently relate to the stated inside diameter. Further, in some instances a physician may elect to use a more rigid catheter for one section of the artificial extravascular conduit system, and a more pliable graft for a different section of the same system.

In any such instances, one or more connectors may be used to couple conduits together to form a luminal pathway. In the case of conduits of different characteristics or sizes, if the connector does not accommodate the various conduits, there may be a disruption in the laminar flow of fluid, e.g., blood, through the system. If the fluid is blood, turbulent flow could lead to extensive complications, including thrombosis, which may have significant negative impact on patient morbidity and mortality. Furthermore, in many instances the type and construction of a desired conduit may depend on patient anatomy, therapy type, doctor preference, and so forth. Ability to connect two conduits using a connector may thus facilitate flexibility before and during procedures by allowing a practitioner to select each conduit according to factors such as those discussed above while maintaining a smooth transition from one conduit to the next via the connector.

As further detailed below, various connectors are within the scope of the present disclosure. Some such connectors may be configured to couple to two separate conduits. Some such connectors within the scope of this disclosure may be configured to be coupled by a practitioner, during therapy, to two separate conduits. Still further, connectors within the scope of this disclosure may be configured to provide a smooth or low-profile interface between conduits to facilitate laminar flow between the conduits.

In the following detailed description, reference is made to the accompanying drawings which form a part hereof and in which are shown, by way of illustration, specific embodiments of the disclosure that may be practiced. These embodiments are described in sufficient detail to enable those of ordinary skill in the art to practice the present disclosure, and it is to be understood that other embodiments may be utilized, and that structural, logical, and electrical changes may be made within the scope of the disclosure. From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

In this description, specific implementations are shown and described only as examples and should not be construed as the only way to implement the present disclosure unless specified otherwise herein. It will be readily apparent to one of ordinary skill in the art that the various embodiments of the present disclosure may be practiced with numerous other vascular access solutions. The devices and methods described herein could be useful in a number of environments that employ conduits used or implanted into the body, such as vascular access systems, ventricular assist devices, total artificial hearts, and various types of hemodialysis systems. It would be apparent to one of ordinary skill in the art that the present disclosure may be practiced in any situation that uses at least one conduit, not just fluid or blood conduits. The environments in which the present disclosure may be practiced include short-term applications, e.g., several days to weeks, and longer-term applications, e.g., months to years.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

While the disclosure is susceptible to various modifications and implementation in alternative forms, specific embodiments have been shown by way of non-limiting example in the drawings and have been described in detail herein. However, it should be understood that the disclosure is not intended to be limited to the particular forms disclosed. Rather, the disclosure includes all modifications, equivalents, and alternatives falling within the scope of the disclosure as defined by the following appended claims and their legal equivalents.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

Referring in general to the following description and accompanying drawings, various embodiments of the present disclosure are illustrated to show its structure and method of operation. Common elements of the illustrated embodiments may be designated with similar reference numerals. Accordingly, the relevant descriptions of such features apply equally to the features and related components among all the drawings. Any suitable combination of the features, and variations of the same, described with components illustrated in FIG. 1, can be employed with the components of FIG. 2, and vice versa. This pattern of disclosure applies equally to further embodiments depicted in subsequent figures and described hereinafter. It should be understood that the figures presented are not meant to be illustrative of actual views of any particular portion of the actual structure or method, but are merely idealized representations employed to more clearly and fully depict the present invention defined by the claims below.

Vascular access systems may be designed and constructed as a single-piece, integrated device, or a multi-piece device comprising separate components that are later joined together. Some embodiments of multi-piece devices are discussed in U.S. Pat. No. 8,690,815 to Porter et al. A multi-piece device may allow an end user, such as a physician, to remove one or more components after they have been implanted in a patient. This may be advantageous if particular components in the vascular access system fail from, for example, thrombus formation or stenosis. It would allow for some components and not the entire vascular access system to be removed. The connectors or interfaces where the separate components of a multi-piece device are joined or attached are potential sources of turbulent flow within the lumen of the system. Any indentation or protrusion into or out of the lumen may cause a disruption of flow. In embodiments in which the multi-piece device is a vascular access system, this turbulent flow may disrupt the normal laminar flow of blood. Disruption in the laminar flow of blood creates a potential risk for thrombus development or hemolysis.

Thus, in some instances, connectors, and the various components of a multi-piece device, are designed to maintain smooth laminar flow, and in some instances improved laminar flow, between components through the connector, and also resist creep or separation of the joined components. Such a connector system may be used with AV grafts, peripherally inserted central catheters (PICC), implantable infusion catheters with and without fluid reservoirs, implantable infusion pumps, left ventricular assist devices, and any other device configured to provide laminar flow from one end of a multi-piece device to the other end of the multi-piece device. In some embodiments this connector is configured to securely couple with the multi-piece vascular access system. In addition to joining fluid conduits, the connector may be used to join conduits to other devices such as reservoirs and needle access ports.

The connector may comprise a biocompatible and/or hemocompatible material. The connector may be used for attaching two conduits which may or may not have different internal and/or outer diameters. In some embodiments, the connector provides a lumen with a smooth fluid path from one end of the multi-piece device to the other. In some embodiments, the connector may have a securing system and/or connecting member to secure a conduit to the connector, which resists disconnection, migration, or separation of the joined components. The connecting member on the connector may be pivotably coupled to a flange on the connector. In some embodiments the connecting member may be any securing device such as clips, rings, sutures, wires, C-shaped clamshell, snap fits, or other mechanical interfits.

In some embodiments, the multi-piece device may comprise a strain relief structure, which is configured to resist occlusion and kinking along portions of a conduit attached to the device. A strain relief structure may be used in connection with any vascular access system including flexible segments such as those comprising polytetrafluoroethylene (PTFE), silicone, polyurethane, or other materials. In some embodiments, one side of a connector may be preconnected to a component of the multi-piece device to the connector before the start of the surgery, for example a connector may be coupled to one conduit before therapy begins. In some embodiments, a procedure may also comprise selecting a suitably sized connector for the conduits chosen by the end user, which may have different internal and/or outer diameters. As further outlined below, in some embodiments an end user is provided with a kit with a plurality of differently sized connectors, or a plurality of different connecting members to be used with various connectors.

In the following discussion, whenever a component is mentioned that has been depicted in the figures with a prime embodiment, e.g., 104 as 104' or 104", any discussion of one embodiment may apply to some or all of the other embodiments.

FIGS. 1A-1E depict various views of individual components and subassemblies of a vascular access system 100 (depicted in FIG. 1B) with connectors and conduits suitable to facilitate blood flow, or flow of any fluid, from one region to another, such as in a human body. FIG. 1A depicts a connector 101 component of the vascular access system 100 which may be configured to couple two conduits (such as conduits 160 and 162 of FIG. 1B) to either a first end 102 or a second end 104 of the connector 101. In some embodiments the vascular access system 100 may be configured to shunt blood from a first vascular lumen to a second vascular lumen. The vascular access system 100 and the connector 101 can take any suitable form, and in some embodiments is configured to be implanted subcutaneously within an animal, in some instances a mammal, such as a human. The connector 101 may be implanted subcutaneously and extravascularly. The connector 101 may be configured to improve or maximize laminar flow through the lumen, and to minimize or eliminate potential turbulent flow through the system, more specifically blood passing through the vascular access system 100. The connector 101 may be configured to join a first artificial conduit, such as 160, with a first outside diameter, to a second artificial conduit, such as 162, with a second outside diameter in such a way that there is a continuous lumen between the two conduits. In an alternative embodiment the first artificial conduit and the second artificial conduit have the same outside diameter. The connector 101 may comprise various forms, such as, but not limited to, a double-sided connector, a clamshell connector, a suture, tension clips, and/or other embodiments discussed in greater detail below. In some embodiments the connector 101 is capable of joining a single artificial conduit. In some configurations, the connector 101 may be extracorporeal.

In some embodiments, the connector 101 comprises a first end 102 with an outside diameter configured to engage with a first end of an artificial conduit. The connector 101 may further comprise a second end 104 and a flange 106. In some embodiments, the flange 106 comprises holes (not shown) through which grasping tools or suture may be passed. In some embodiments, the connector 101 may comprise connecting members 120 and 122. In some embodiments, the connecting member 120 may comprise a first securing device 108 pivotably coupled with the flange 106 and a second securing device 110 pivotably coupled with the flange 106, such that the two securing devices 108 and 110 are configured to close over the first end 102 of the connector 101 to securely fasten at least one conduit, such as conduit 160 to the connector 101. In some embodiments there is no taper from the first end 102 of the connector 101 to the second end 104; instead, the inside diameter of the lumen remains constant throughout the length of the connector 101.

In some embodiments, the connector 101 comprise ridges 116 and 118 on the body of the connector 101 closest to the flange 106. These ridges 116 and 118 are configured to more securely hold the conduit when an end user slides it onto the first end 102 or the second end 104 of the connector 101. In some embodiments, the first connecting member 120 and the second connecting member 122 are configured to close over artificial conduits after the end user slides at least one conduit over first end 102 or the second end 104 of connector 101. Connecting members 120 and 122 are configured to compress the conduit against ridges 116 or 118 to create more engagement with the connector 101.

In some embodiments the end user can continue to push the conduit past the ridges 116 until the conduit abuts against the flange 106. The end user can then close the securing devices 108 and 110 to compressibly engage the conduit and secure it to the connector 101. In some embodiments the connector 101 is configured to couple to both a conduit and a strain relief structure (not shown). The strain relief structure is configured to reduce or minimize kinking or pinching of the conduit. In some embodiments conduits 160, 162, and/or 164 (depicted in FIGS. 1B and 1C) lack any beading or added layers such as polytetrafluoroethylene (PTFE) to the inner or outer surface in the portions nearest to the connector 101.

The vascular access system may comprise a plurality of different sized connectors 101 or connecting members 120 and 122 configured to apply compressive force to sandwich a plurality of different sized outside diameter conduits and different sized outside diameter strain relief structures. In some instances, the inside diameter of a given conduit does not correspond one-to-one with the outside diameter depending on the brand, manufacturer, or material of the conduit.

In some embodiments the securing devices 108 and 110 of connecting member 120 can be configured to irreversibly engage with one another using engaging teeth 150 and 152 to clamp down around the conduit. In a similar fashion, the end user can slide a conduit over the second end 104 and form a friction bond with ridges 118 until the conduit abuts against the flange 106. The end user can then similarly close securing devices 112 and 114 of connecting member 122 to compressibly engage the conduit and secure it to the connector 101 at the second end 104. In some embodiments, the securing devices 112 and 114 can be configured to irreversibly engage with one another using the engaging teeth 154 and 156 to clamp down around the conduit.

In some embodiments the securing device may be opened after it has been closed to compressibly engage the conduit as described above. Various embodiments of a reversible securing device are discussed in greater detail below. In some embodiments the securing device is configured to compressibly engage conduits with varying outside diameters. This would allow an end user, such as a physician, to elect to use varying conduits of different design or manufacture, or manufactured using different materials which may be rigid or pliable depending on the specific needs. Once coupled to the connector 101, these conduits would form a continuous lumen from one conduit to the next. By accommodating numerous conduits with varying outside diameters, the securing device of the connector 101 allows the end user to focus on clinical decisions on which conduits to use, with no limitation from the connector 101 and the securing device.

In some embodiments the securing device does not rely on compression on one or both sides of the connector 101; these embodiments will be discussed in greater detail below. In some embodiments the connector 101 provides a mechanical friction coupling system, such as that provided by ridges 116 and 118 without the compression from the securing device depicted in FIG. 1A. In some embodiments the end user can suture or otherwise couple the conduit to the connector 101. In some embodiments one of the conduits comes pre-coupled to one end of the connector 101.

In some embodiments, the artificial conduits are configured to be accessed for hemodialysis. In other words, during some medical procedures (e.g., hemodialysis), the conduits 160, 162, and/or 164 may be accessed in lieu of the natural vasculature of a patient. In some embodiments, the conduits 160, 162, and/or 164 comprise and/or consist of PTFE, such as expanded PTFE (ePTFE), rotational spun PTFE, or electrospun PTFE. In some embodiments, the conduits 160, 162, and/or 164 comprise silicone. In some embodiments, the conduits 160, 162, and/or 164 comprise a fibrous polymer.

In some embodiments, the conduits 160, 162, and/or 164 include a puncturable and self-sealing wall such that the wall may be punctured by insertion of a needle and then reseal upon withdrawal of the needle. The self-sealing wall may be of any suitable composition. In some embodiments, the self-sealing wall is a multi-layered construct. For example, some embodiments include an outer layer, an inner layer, and at least one tie layer disposed between the outer layer and the inner layer. In some embodiments, one or more of the outer layer and the inner layer comprise PTFE. For example, the outer layer may comprise or consist of expanded PTFE, while the inner layer comprises and/or consists of rotational spun or electrospun PTFE. In some embodiments, the tie layer comprises an elastomer, such as elastomeric silicone. Due, at least in part, to the properties of the silicone, the resulting construct may be self-sealing. In other words, when a needle that has been inserted through the wall is withdrawn from the conduits 160, 162, and/or 164, the wall may seal itself, thereby preventing leakage of blood from the conduits 160, 162, and/or 164.

In some embodiments the connector 101 comprises and/or consists of layers on the inside diameter, such as a luminal layer of silicone, or luminal layering of PTFE, such as expanded PTFE (ePTFE), rotational spun PTFE, or electrospun PTFE. In some embodiments the inside layering of the lumen of the conduits comprises the same material as the inside layering of the lumen of the connector 101. In some embodiments the lumen of the connector 101 is coated with PTFE, such as expanded PTFE (ePTFE), rotational spun PTFE, or electrospun PTFE prior to sintering to improve adherence of the PTFE to the luminal wall. Still further, any of these materials may be disposed on an outside surface of the connector 101 to as a tissue contact layer on the outside surface.

In some embodiments the conduits are configured to be impermeable in the portion of the conduit closest to the connector 101. In some embodiments the one or more of the outer and the inner layers of the conduit comprises impermeable material for a portion of the conduit that is closest to the portion coupled to the connector 101.

In some embodiments, one or both of the inner surface, the luminal layer, and the outer surface, the abluminal layer, of any one of the components of the vascular access system may be associated with a therapeutic agent. In other words, the therapeutic agent may be disposed on or embedded within a surface of the vascular access system. The therapeutic agent may be released from the surface(s) of the vascular access system to deliver a therapeutically effective dose of the therapeutic agent to the patient when the vascular access system is implanted within a patient. In some embodiments, a first therapeutic agent is associated with the inner surface of the vascular access system and a second therapeutic agent that differs from the first therapeutic agent is associated with the outer surface of the vascular access system. In such embodiments, both the first therapeutic agent and the second therapeutic agent may be delivered into the bloodstream of the patient in therapeutically effective doses when the vascular access system is implanted within the patient. In some embodiments, heparin is used as a therapeutic agent. In some embodiments, the therapeutic agent reduces thrombus or tissue proliferation. In some embodiments, one or both therapeutic agents may be delivered to the abluminal tissues surrounding the implanted vascular access system to either reduce tissue proliferation and/or enhance tissue incorporation, which may enhance early cannulation of the vascular access system.

The vascular access system may be used in any suitable medical procedure, such as to establish vascular access for hemodialysis. For example, where an arteriovenous graft has become occluded or otherwise failed, an alternative artificial flow path that bypasses the occlusion or failure may be established. For example, an artificial flow path may be established from a portion of the arteriovenous graft that is upstream of the occlusion or failure in the arteriovenous graft to the right atrium of the heart.

Figure 1B:
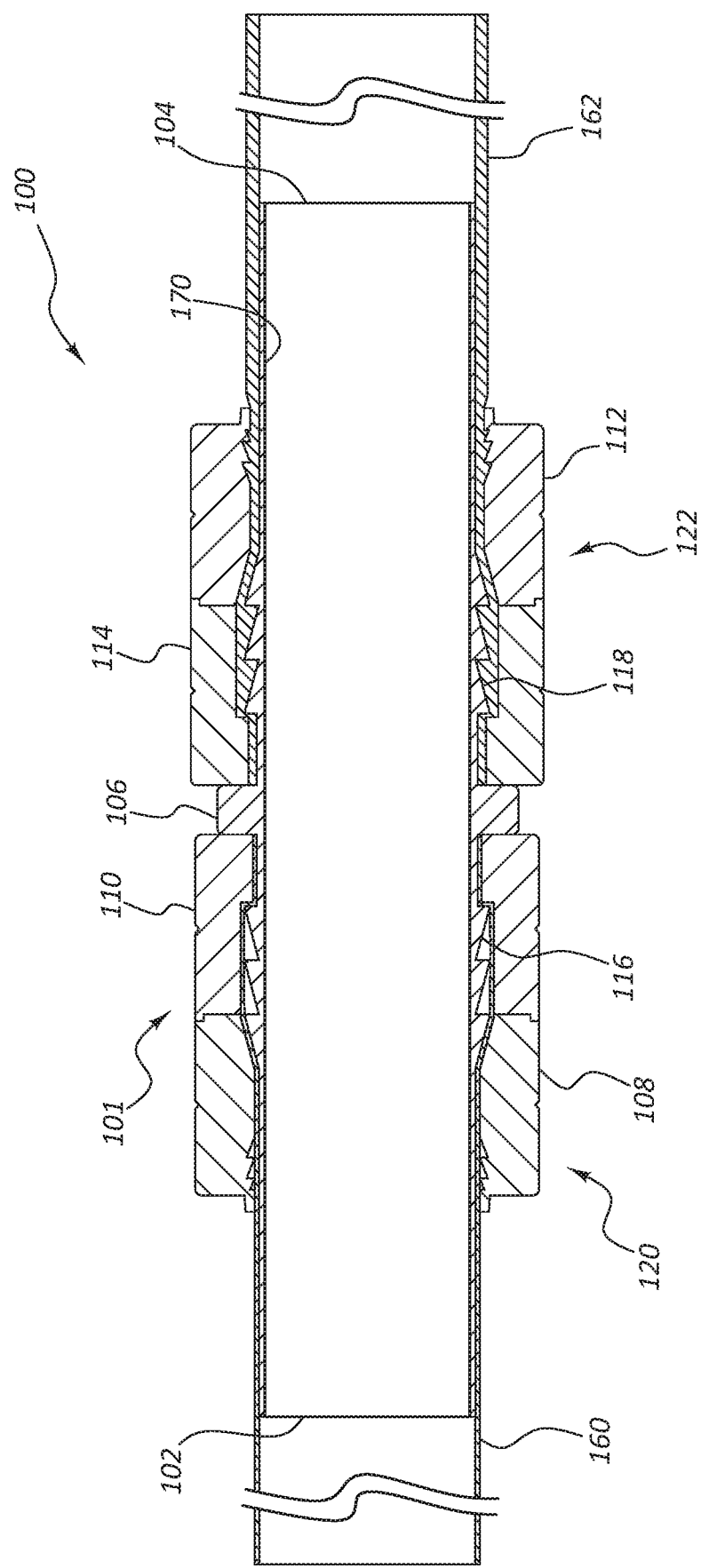
FIG. 1B is a simplified cross-section view of certain components of a vascular access system including components of the system of FIG. 1A.

FIG. 1B depicts a simplified cross-section view of the vascular access system 100 comprising the connector 101 coupled to a first conduit 160 and a second conduit 162. The connecting member 120 is depicted closed around the conduit 160 and compressed against ridges 116. The connecting member 122 is depicted closed around the conduit 162 and compressed against ridges 118. The connector 101 can take any suitable form, and in some embodiments is configured to be implanted subcutaneously within a patient. The connector 101 may be implanted subcutaneously and extravascularly. The connector 101 is configured to improve laminar flow through the lumen. In some embodiments the connector 101 is configured to couple to conduits with varying outside diameters in such a way as to maintain a continuous lumen between the two conduits, such as conduits 162 and 160. As used herein, a "continuous lumen" includes embodiments wherein the lumen extending between the conduits 162 and 160 may or may not include a luminal surface that has seams or joints (for example at the joints between the conduits 162 and 160 and the connector 101) while maintaining an otherwise uninterrupted luminal surface. The connector 101 comprise various forms, such as, but not limited to, a double-sided connector, a clamshell connector, a suture, tension clips, and/or other embodiments discussed in greater detail below. In some embodiments the connector 101 is capable of joining a single artificial conduit.

In the illustrated embodiment, the connector 101 comprises the first end 102 with an outside diameter configured to engage with a first end of an artificial conduit 160. The connector 101 may further comprise the second end 104 and the flange 106. In some embodiments, the flange 106 comprises holes (not shown) through which grasping tools or suture may be passed. In some embodiments, the connector 101 may comprise connecting members 120 and 122. In some embodiments, the connecting member 120 may comprise the first securing device 108 pivotably coupled with the flange 106 and the second securing device 110 pivotably couple with the flange 106, such that the two securing devices 108 and 110 are configured to close over the first end 102 of the connector 101 to securely fasten at least one conduit 160 to the connector 101. In some embodiments, the connecting member 122 may comprise the first securing device 112 pivotably coupled with the flange 106 and the second securing device 114 pivotably couple with the flange 106, such that the two securing devices 112 and 114 are configured to close over the second end 104 of the connector 101 to securely fasten at least one conduit 162 to the connector 101.

In some embodiments the securing devices 108 and 110 can be configured to irreversibly engage with one another using the engaging teeth 150 and 152 (as depicted in FIG. 1A) to clamp down around the conduit 160. In a similar fashion, the end user can slide a conduit 162 over the second end 104 and form a friction bond with ridges 118 until the conduit abuts against the flange 106. The end user can then similarly close the securing devices 112 and 114 to compressibly engage the conduit and secure it to the connector 101 at the second end 104. In some embodiments, the securing devices 112 and 114 can be configured to irreversibly engage with one another using the engaging teeth 154 and 156 (as depicted in FIG. 1A) to clamp down around the conduit 162. In some embodiments there is no taper from a first end 102 of the connector 101 to the second end 104; instead, the inside diameter of the lumen remains constant throughout the length of the connector 101.

In some embodiments the connector 101 has a coating 170 on the luminal side of the connector 101. In some embodiments the coating 170 comprises silicone, or PTFE, such as expanded PTFE (ePTFE), rotational spun PTFE, or electrospun PTFE. In some embodiments the inside diameter is coated with the same material as the material that comprises the conduits 160, 162, and/or 164. In some embodiments the lumen of the connector 101 is coated with PTFE, such as expanded PTFE (ePTFE), rotational spun PTFE, or electrospun PTFE prior to sintering to improve adherence of the PTFE to the luminal wall.

Figure 1D:
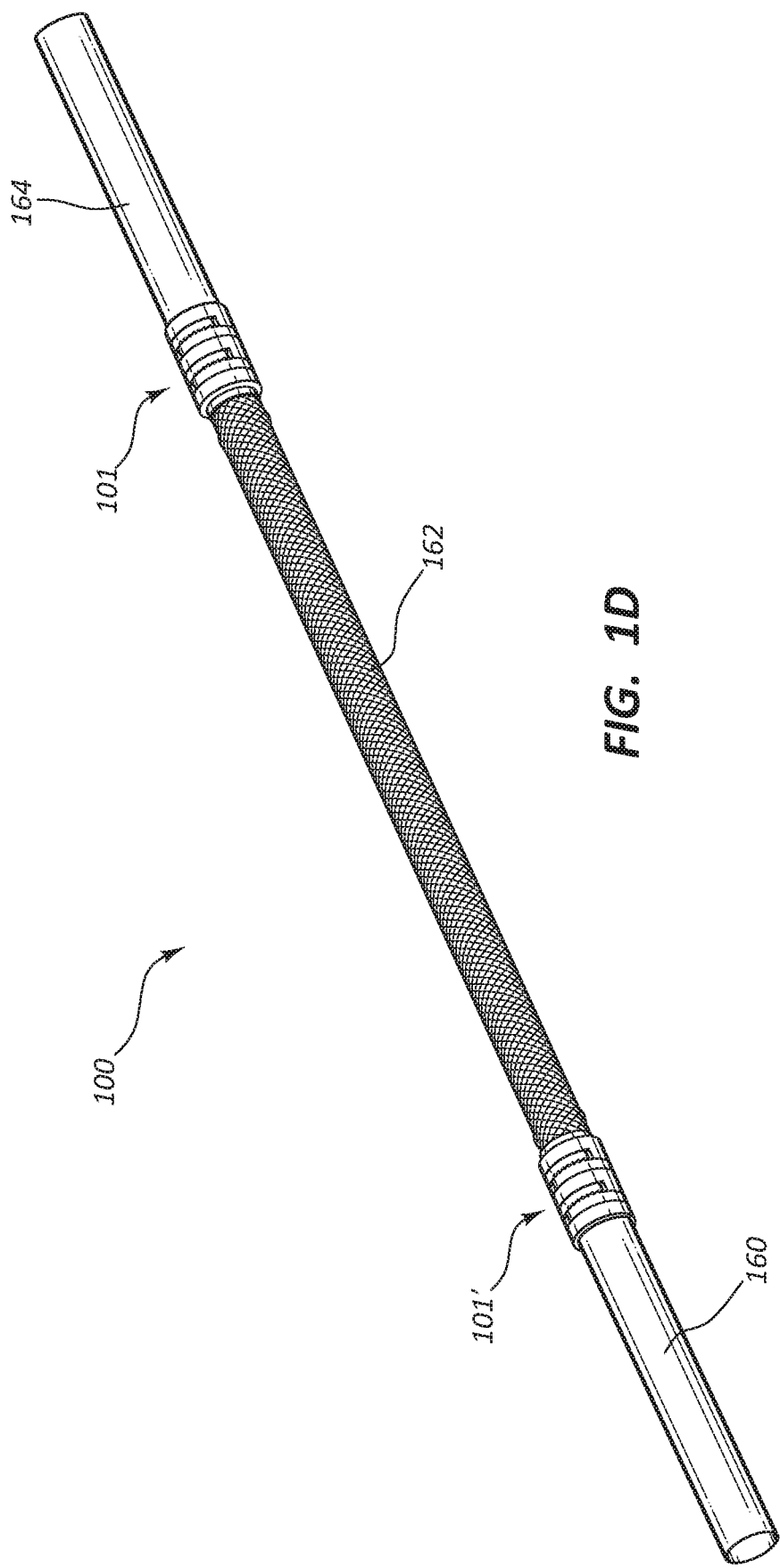
FIG. 1D is a simplified perspective view of certain components of the vascular access system of FIG. 1C, in a second configuration.

FIG. 1C depicts one embodiment of a vascular access system 100 in which the connector 101 and a connector 101' couple the conduits 160, 162, and 164 together into a continuous lumen. In some embodiments the conduits 160, 162, and 164 are formed of the same materials. In some embodiments any one of the conduits 160, 162, and 164 may be composed of different materials. Stated differently in some embodiments one conduit, such as the conduit 162, may be made of different materials than the conduits 160 and 164. In some embodiments the conduits 160 and 164 are made from relatively flexible materials. In some embodiments the conduits 160 and 164 may be made of materials that are suitable for anastomosis to a blood vessel in a mammalian body, such as an artery or vein in a human body. The length of the conduits 160, 162, and 164 may all vary in length as is determined by the end-user, based on such facts as desired location in the body of, for example, a patient and the particularities of the anatomy of the subject. In some embodiments the vascular access system as depicted in, for example, FIG. 1C may have lengths that facilitate the bypass of a narrowed, obstructed, and/or damaged portion of an artery or vein. In some embodiments the conduit 162 may be replaced with a needle access port (not depicted). FIG. 1D depicts an embodiment in which the connectors 101 and 101' have been closed around the conduits 160, 162, and 164. As will be discussed in further detail below the connector may be reversibly closed or, in the alternative, irreversibly closed.

Figure 1E:
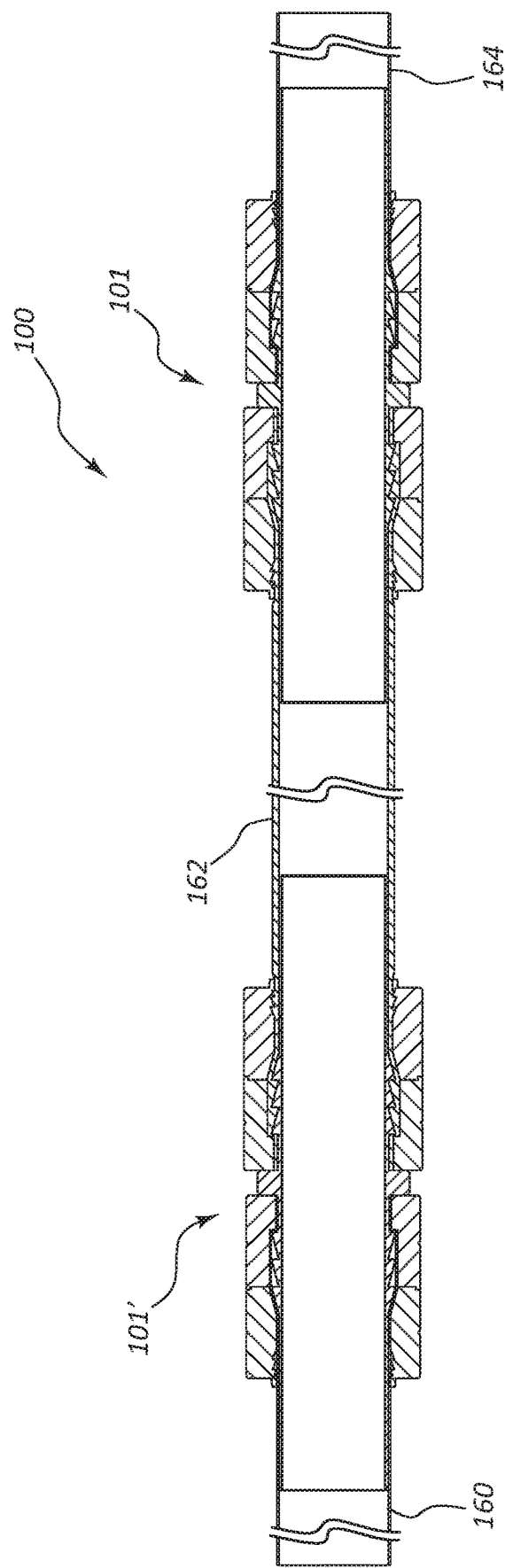
FIG. 1E is a simplified cross-section view of certain components of the vascular access system of FIG. 1D.

In some embodiments, the conduits 160, 162, and 164 comprise multiple layers, as is depicted in cross-sectional view in FIG. 1E. The cross-sectional view of FIG. 1E depicts an inner luminal layer of the conduits 160, 162, and 164 which may be formed from PTFE, such as expanded PTFE or fibrous PTFE. In some embodiments in which fibrous PTFE is used, the fibrous PTFE may be formed by rotation of a spinneret, in other words, rotational spun PTFE, and/or by subjecting a solution or dispersion comprising PTFE to an electric field, in other words, electrospun PTFE. In some embodiments the luminal layer is configured to permit tissue ingrowth.

In some embodiments the conduits 160, 162, and 164 comprise an outer layer which may have a composition identical to the inner layer as discussed above. In an alternative embodiment the outer abluminal layer differs in composition from the inner luminal layer. In some embodiments any one of the conduits 160, 162, and 164 may be made of fibrous fluorinated ethylene propylene (FEP). In alternative embodiments any one of the conduits 160, 162, and 164 is composed of silicone, FEP, and/or polyether block amide (e.g., PEBAX).

In some embodiments any one of the conduits 160, 162, and 164 may include a porous tube (not depicted) which may be partially or completely disposed between the inner luminal layer and the outer abluminal layer. In some embodiments, the porous tube may be disposed between or embedded within one or more layers of polymer. The porous tube may strengthen or reinforce any one of the conduits 160, 162, and 164, as it may be designed to increase the crush force of the conduit. In some embodiments the porous tube is made of a metal alloy. In some embodiments the porous tube may be made of a nickel-titanium alloy, such as nitinol. In some embodiments the porous tube is formed by helically winding nitinol, by braiding nitinol, or by laser-cutting nitinol. In some embodiments the porous tube may have different properties at different sections of the tube. For example, the porous tube may have a lower crush force at the proximal end than at the distal end. In some embodiments the nitinol may be less dense in some segments of the tube than in other. In some embodiments different segments of the tube may be configured to facilitate anastomosis to a vessel in a mammal, such as a human patient.

In some embodiments, any one of the conduits 160, 162, and 164 and connectors 101 and 101' may be coated on the abluminal layer with a first or second therapeutic agent, as discussed above. In some embodiments, any one of the conduits 160, 162, and 164 and connectors 101 and 101' may be coated on the luminal surface with an identical material, and/or different materials, as is discussed above. In some embodiments, the therapeutic agent reduces thrombus or tissue proliferation. In some embodiments, one or both therapeutic agents may be delivered to the abluminal tissues surrounding the implanted vascular access system to either reduce tissue proliferation and/or enhance tissue incorporation, which may enhance early cannulation of the vascular access system. In some embodiments, any one of the conduits 160, 162, and 164 may have a smooth and nonporous exterior surface. The exterior surface may prevent tissue ingrowth, thereby enabling replacement of the conduit.

The connectors 101 and 101' as well as any one of the conduits 160, 162, and 164, may be configured to improve or maximize laminar flow through the lumen, and to minimize or eliminate potential turbulent flow through the system, more specifically blood passing through the system. The vascular access system 100 as depicted in FIGS. 1D and 1E may be planted subcutaneously and extravascularly. In some embodiments any one of the conduits 160, 162, and 164 may be manufactured pre-coupled with a connector such as the connectors 101 and 101'. The vascular access system 100 as depicted in FIGS. 1D and 1E may be used extracorporeally.

In some embodiments connectors, such as 101, have two ends configured to be manipulated, secured, and in some embodiments reopened by an end user, such as a physician during treatment of a patient. Each end of a connector, such as 101, is configured to couple with at least one artificial conduit, and in some embodiments multiple conduits of varying pliability, inside diameter, and outside diameter, to form a fluid-tight lumen between the artificial conduit and the connector. In some embodiments the connector may comprise more than two ends, to facilitate coupling with more than two artificial conduits, ports, or other devices to provide vascular access to a patient. It is within the scope of this disclosure for the connector to comprise multiple ends each configured to be manipulated, secured, and reopened by an end user. In some embodiments the connector itself provides vascular access for an end user.

In some embodiments there is no taper between one end of the connector and the second end, the lumen within the connector maintains a constant inside diameter. In some embodiments the connector is configured to provide for smooth laminar flow from one end to the second end after each of the two ends has been coupled to artificial conduits. In some embodiments the inside diameter of the connector, such as 101, has a coating layer 170 comprising the same material as one or both of the artificial conduits coupled to it.

In some embodiments the vascular access system is provided for an end user in a kit which may include, for example: a plurality of conduits and a plurality of connectors for coupling conduits. In some embodiments the kit may further include instructions for use and implantation of the vascular access system. In some embodiments the kit and/or related components described above may be used to establish a subcutaneous, extravascular continuous lumen that may bypass an occluded, partially occluded, or damaged portion of vasculature in a mammal, such as a human patient.

FIGS. 2-4, 5A, 6A, 7-9, and 16 depict alternative embodiments of connectors which can be used to couple one or two conduits to form a continuous lumen from one conduit to another. In the embodiments depicted in these figures the connecting member may be any securing device such as clips, rings, sutures, wires, C-shaped clamshell, snap fits, or other mechanical interfits.

Figure 2:
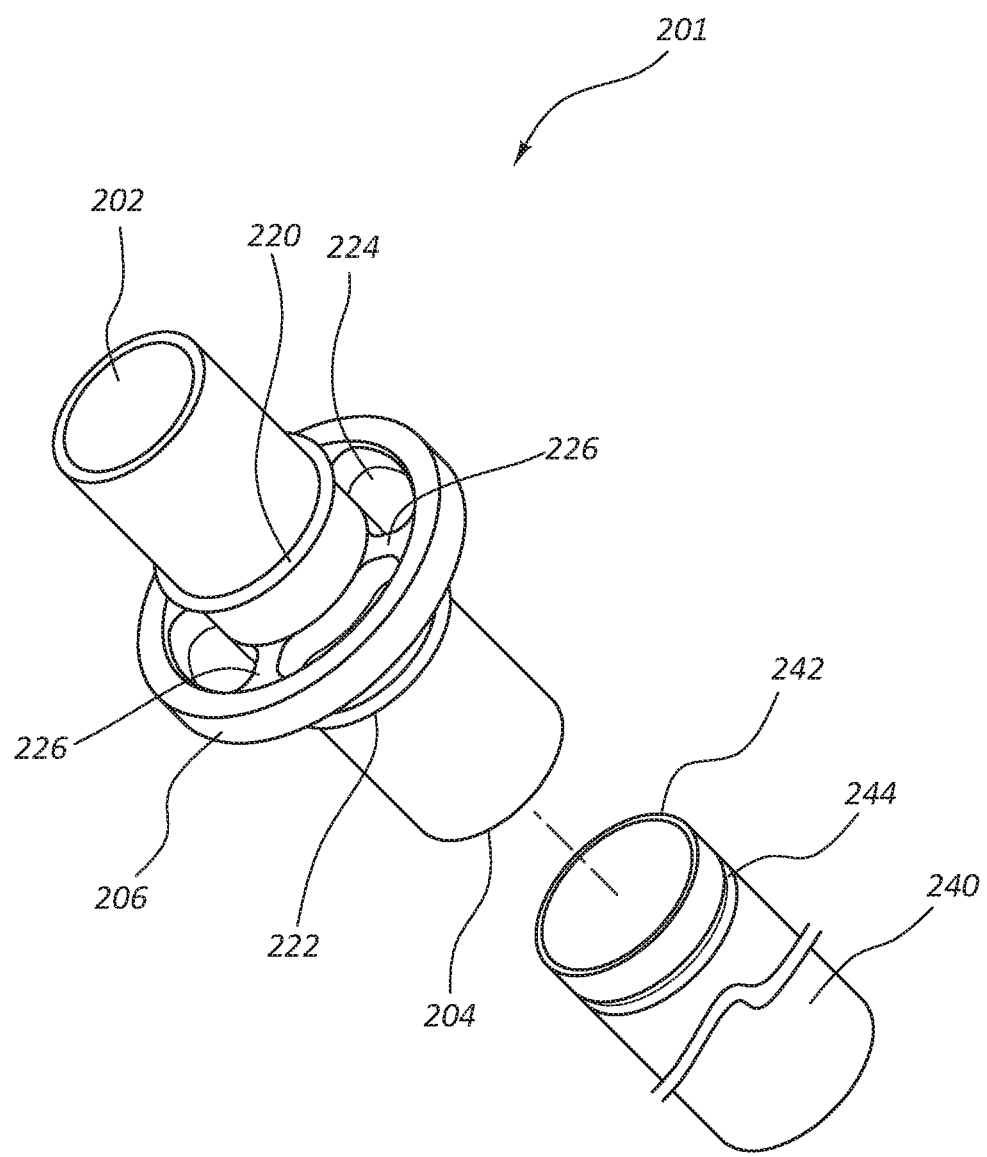
FIG. 2 is a simplified perspective view of certain components of a vascular access system.

FIG. 2 depicts an embodiment of a connector 201 that resembles the connector 101 described above in certain respects. Accordingly, like features are designated with like reference numerals, with the leading digit increased to "2." For example the flange 106 from any one of FIGS. 1A through 1E may, in some respects, resemble a flange 206 from FIG. 2. Relevant disclosure set forth above regarding similarly identified features thus may not be repeated hereafter, but will be understood by a person of ordinary skill in the art to describe an alternative embodiment of the feature. In addition, specific features depicted in any of the figures may not be shown in every figure or identified by a reference numeral in the drawings or specifically discussed in the written description that follows. However, such features may clearly be the same, similar, or substantially the same, as features depicted in other embodiments and/or described with respect to such embodiments. Accordingly, the relevant descriptions of such features apply equally to the features in the following figures. This pattern of disclosure applies equally to further embodiments depicted in subsequent figures and described hereafter, wherein the leading digit may be further increased. Any suitable combination of the features, and variations of the same, can be employed with any of the following embodiments.

In the embodiment depicted in FIG. 2, the connector 201 comprises a first end 202, a second end 204, and a built-in o-ring 220 and 222 which is configured to fit into a groove 244 pre-manufactured into a conduit 240. The end user would slide the first end 242 of conduit 240 over a second end 204 of the connector 201 until the o-ring 222 engages the groove 244 to seal the conduit 240 to the connector 201. In this and other embodiments described below this o-ring 222 may be configured to couple the conduit 240 to the connector 201 reversibly or irreversibly. The benefits of reversibly coupling the conduit 240 to the connector 201 would enable an end user to replace any one of the multiple components of a vascular access system implanted into a patient if one should fail. In some embodiments the flange 206 may be configured with openings 224 and radial brackets 226 to enable the end user to slide sutures or tools through the flange 206 to further facilitate coupling the conduit 240 to the connector 201.

Figure 3:
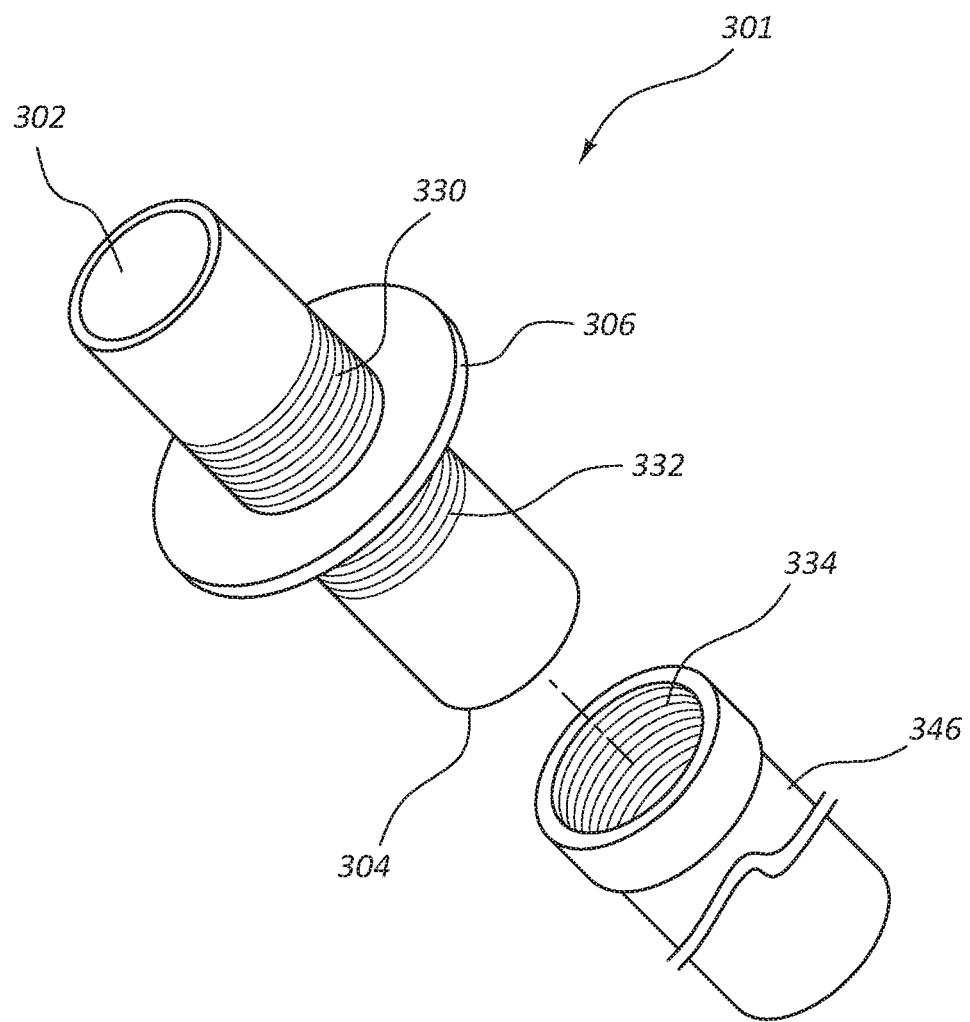
FIG. 3 is a simplified perspective view of certain components of a vascular access system.

FIG. 3 depicts an embodiment of a connector 301 in which a first end 302 and a second end 304 is configured with threading 330 and 332 on either side of flange 306. Threading 332 is configured to reversibly couple a conduit 346 with a threaded nut 334 onto second end 304 of connector 301. Similarly, threading 330 is configured to reversibly couple another conduit (not depicted) with a threaded nut (not depicted) similar to threaded nut 334 onto first end 302 of connector 301. The conduits such as conduit 346 will slide over the second end 304 and the threaded nut 334 will engage threading 332. The end user can then couple the conduits such as conduit 346 until it abuts against flange 306. The threaded nuts such as threaded nut 334 may be configured to irreversibly couple the conduits, such as conduit 346 to the connector 301.

Figure 4:
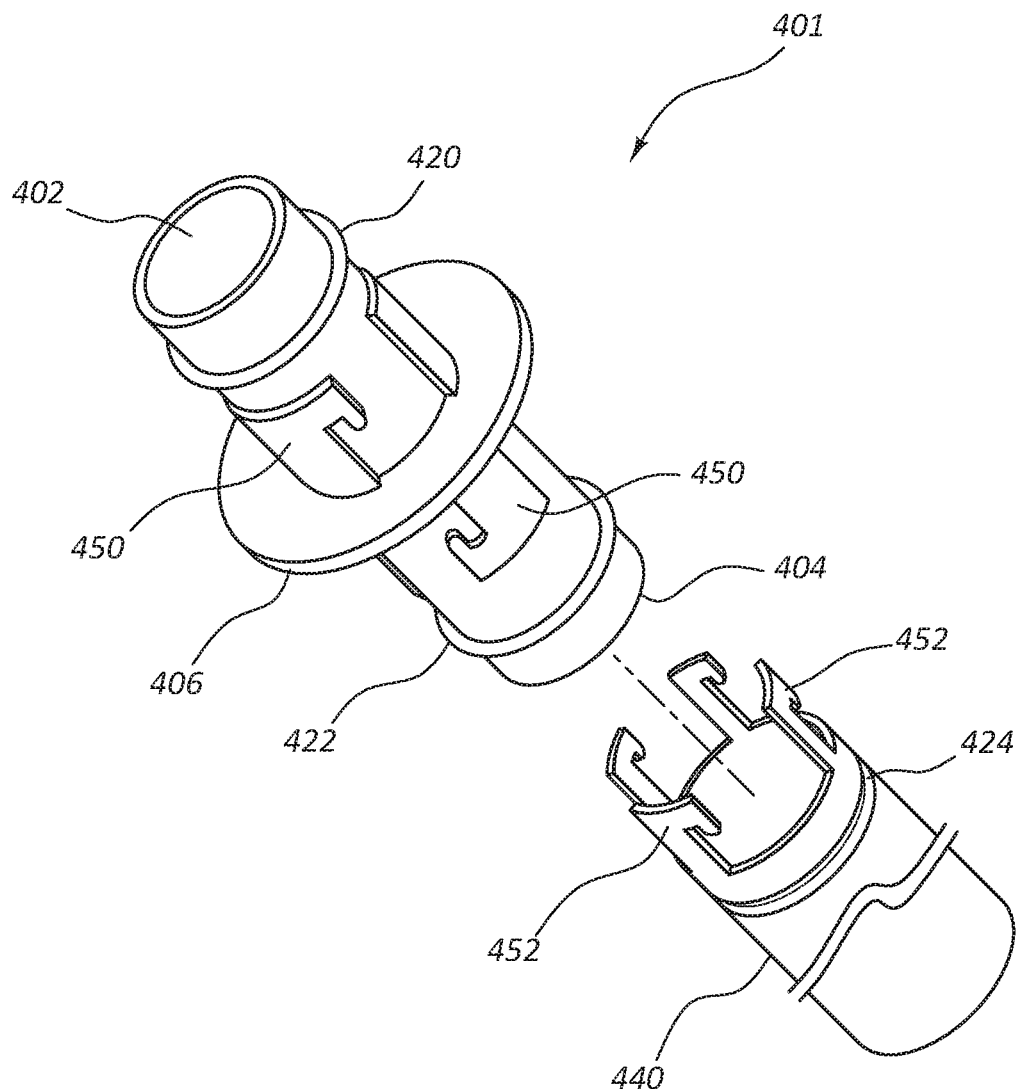
FIG. 4 is a simplified perspective view of certain components of a vascular access system.

With regard to FIG. 4, this illustration depicts an embodiment of a connector 401 with a first end 402 and a second end 404. Here the connecting member is a series of connector interfits 450 with a built-in seal, such as an o-rings 420 and 422 configured to couple with a groove 424 on conduit 440. In some embodiments conduit 440 comprises conduit interfits 452 configured to engage connector interfits 450. The end user can engage the conduit interfits 452 with the connector interfits 450 and twist to lock them together. A flange 406 and a seal, such as an o-ring 422 and groove 424, are configured to enhance the fluid-tight seal between the conduit 440 and the connector 401. In some embodiments the coupling of the conduit 440 and the connector 401 with the interfits 452 and 450 is irreversible. In some embodiments the coupling of the conduit 440 and the connector 401 with the interfits 452 and 450 is reversible. In some embodiments a locking mechanism (not depicted) allows an end user to disengage the interfits 452 and 450 to disengage the conduit 440 from the connector 401.

FIG. 5A depicts vascular access system 500 comprising connector 501 with a first end 502, a second end 504, and flange 506. In some embodiments the connector 501 is configured to have ridges 562 and 564 to provide a friction bond with a conduit, such as a conduit 540. In some embodiments the connector 501 has a connecting member 560 configured to engage with conduit end 552 to snap the conduit 540 in place and provide for a fluid-tight seal. In some embodiments the connecting member 560 has a ridge configured to snap over a raised conduit end 552. The conduit 540 with a raised end 552 can be pushed over the first end 502 of the connector 501. The ridges 564 would provide friction coupling as the end user continues to slide the conduit 540 onto the connector 501. The raised end 552 of the conduit 540 may pass into the connecting member 560 which would deflect outward with added pressure from the end user pushing the conduit 540 into place until snaps 566 (depicted in FIG. 5B) of the connecting member 560 engage the raised end 552 of the conduit 540, providing a fluid-tight seal between the conduit 540 and the connector 501. In a similar embodiment the connector 501 has a connecting member 560 configured to engage with conduit end 554 to snap the conduit 546 in place and provide for a fluid-tight seal. In some embodiments the connecting member 560 has a ridge configured to snap over a raised conduit end 554. The conduit 546 with a raised end 554 can be pushed over the second end 504 of the connector 501. The ridges 562 would provide friction coupling as the end user continues to slide the conduit 546 onto the connector 501. The raised end 554 of the conduit 546 may pass into the connecting member 560 which would deflect outward with added pressure from the end user pushing the conduit 546 into place until snaps 566 of the connecting member 560 engage the raised end 554 of the conduit 546, providing a fluid-tight seal between the conduit 546 and the connector 501. In some embodiments the connecting member 560 would be made of a strong flexible material that will provide some deflection without cracking.

FIG. 5B depicts a cross-section of an embodiment of the connector 501 before any conduits have been coupled to it. The connecting member 560 is attached to a flange 506, and snaps 566 are near the end of the connecting member 560 as depicted. In some embodiments the connector 501 will also be configured with raised ridges 562 and 564 to provide further friction engagement with the conduits as the end user slides them onto the connector 501.

Figure 5C:
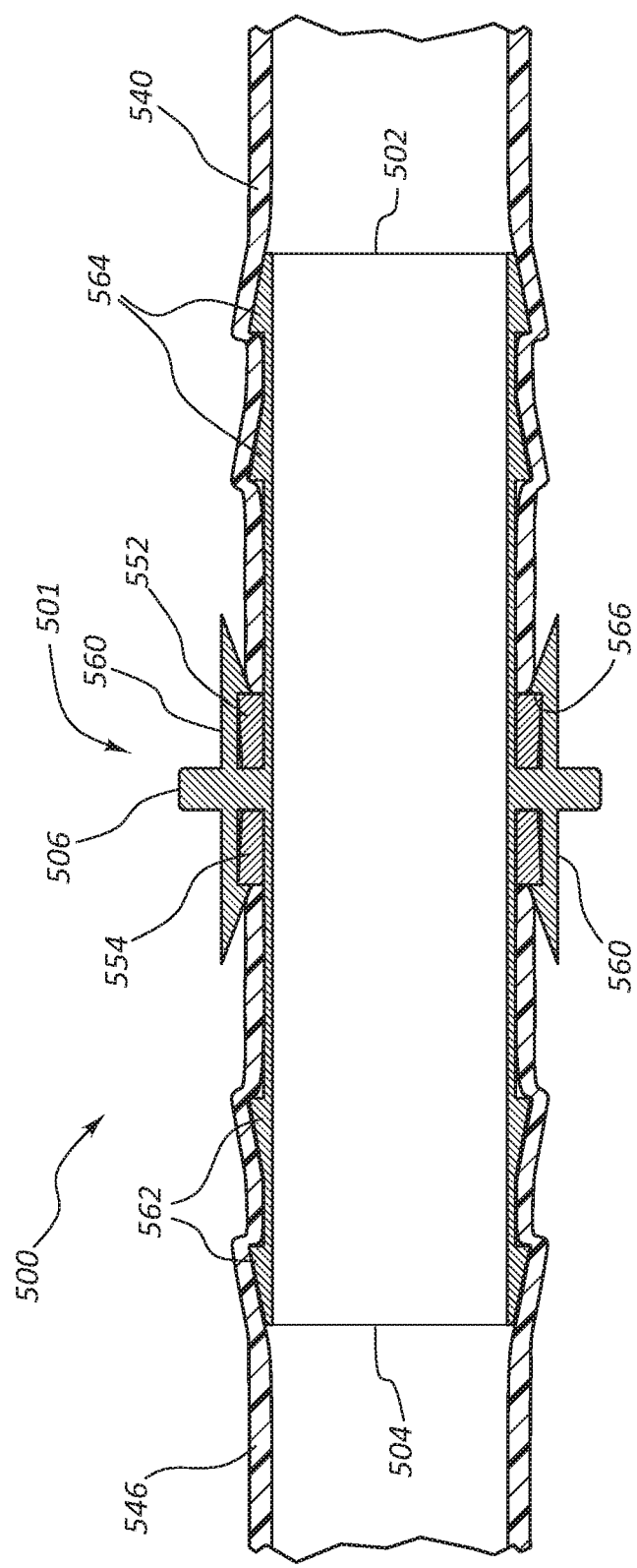
FIG. 5C is a simplified cross-section view of certain components of the vascular access system of FIG. 5A.

FIG. 5C depicts a cross-section vascular access system 500 comprising connector 501 with first end 502, second end 504, and flange 506, after conduits 540 and 546 have been coupled to it. In some embodiments the conduits 540 and 546 have a raised ends 552 and 554 respectively configured to engage with the snaps 566 of the connecting member 560 coupled to flange 506 of the connector 501. As the end user slides the conduit onto the connector 501 the raised end 552 or 554 would deflect the connecting member 560 outward until the raised end 552 slides past snaps 566. In some embodiments the conduits 540 and 546 would be irreversibly coupled to the connector 501 after the snaps 566 engage the raised ends 552 and/or 554 of the conduits 540 and/or 546. In some embodiments the connecting member 560 would allow for a reversible bond with the conduits 540 and 546. In some embodiments the connector 501 does not have raised ridges 562 and 564. In some embodiments the connecting member 560 may have more than one set of engaging snaps, such as 566. In some embodiments the connecting member 560 extends the entire length of the connector 501.

FIG. 6A depicts vascular access system 600 comprising connector 601 with a flange 606, a first end 602 and a second end 604. In some embodiments the connector 601 is configured to comprise a seal, such as an o-ring 620 on inner portion 622. In some embodiments the connector 601 has a connecting member 660 comprising connector interfits 650. Connecting member 660 configured to couple conduit 640 in place and provide for a fluid-tight seal with connector 601. In some embodiments the connecting member 660 is configured to engage connector interfits 650 with conduit interfits 652. The conduit 640 with a first end 656 with first edge 654, and conduit interfits 652 can be pushed over the second end 604 of the connector 601 until it abuts against a flange 606. A first edge 654 of the conduit first end 656 would slide over the second end 604 of the connector 601. In some embodiments the end user could then twist the conduit 640 to snap interfits 652 and 650 together. In some embodiments the engagement of interfits 652 and 650 is irreversible. In some embodiments the engagement of interfits 652 and 650 is reversible. In some embodiments the conduit 640 would be configured with a collar 658 configured to stabilize interfits 652 on the conduit 640.

FIG. 6B depicts a cross-section of an embodiment of the connector 601 with first end 602 and second end 604 before any conduits have been coupled to it. The connector interfits 650 are attached to the flange 606. In some embodiments the connector 601 will also be configured with a seal, such as the o-ring 620 on inner portion 622, to enhance the fluid-tight connection between the conduit 640 and the connector 601.

In some embodiments the interfits 650 of the connecting member 660 (depicted in FIG. 6A) span the entire length of the connector 601 as depicted.

Figure 6C:
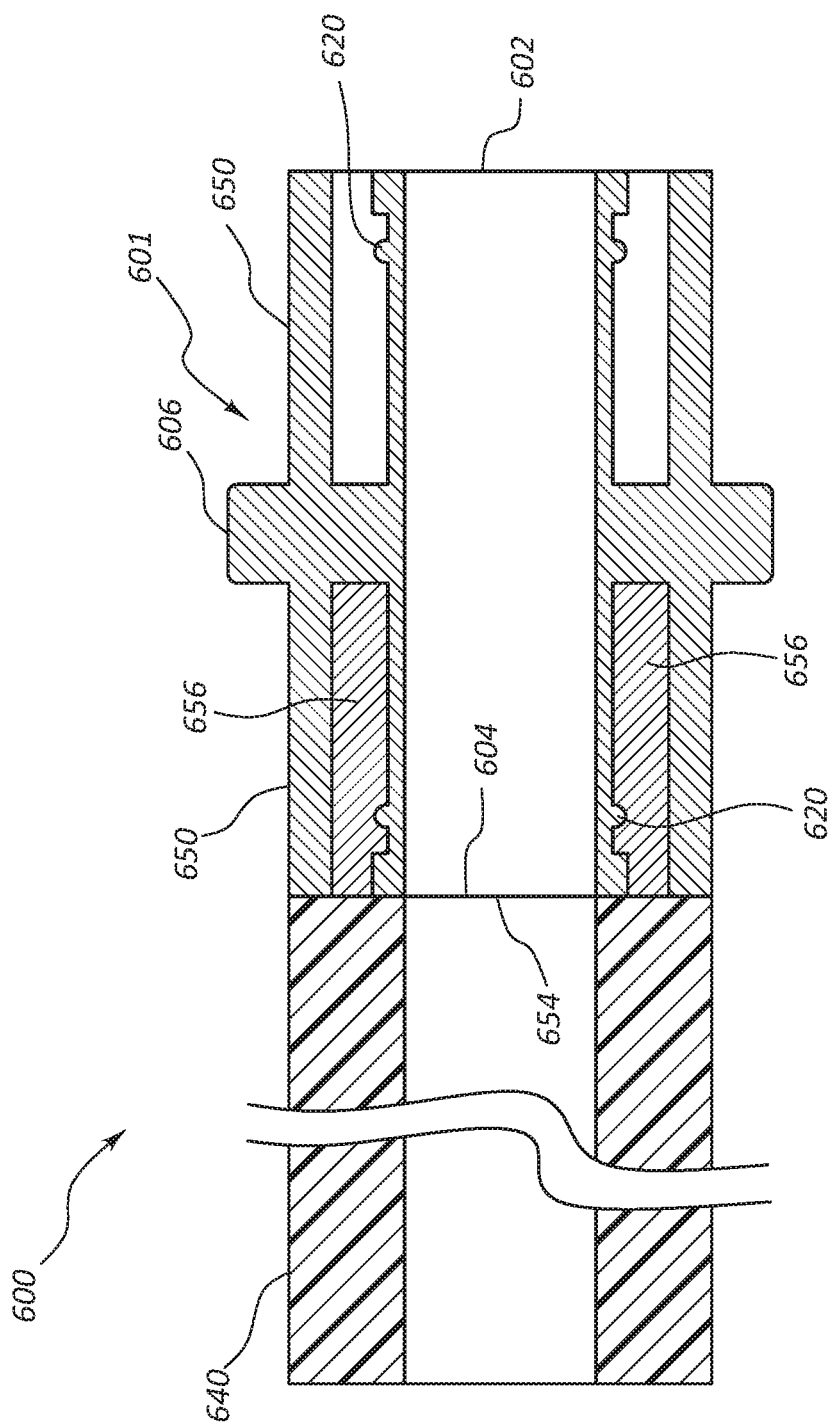
FIG. 6C is a simplified cross-section view of certain components of the vascular access system of FIG. 6A.

FIG. 6C depicts a cross-section of vascular access system 600 comprising connector 601 with first end 602 and second end 604 after the first edge 654 of conduit 640 has been coupled to it. In some embodiments the first end 656 of the conduit 640 would slide onto the connector 601 under the connecting member 660 (depicted in FIG. 6A), engaging the o-ring 620. As the end user slides the conduit 640 onto the connector 601 the interfits 650 would engage the conduit interfits 652. The end user would slide the conduit 640 onto the connector 601 until it abuts against the flange 606. In some embodiments the end user could then twist the connector 601 and/or the conduit 640 to engage the interfits 650 and 652 with one another. In some embodiments the conduit 640 would be irreversibly coupled to 601 after the interfits 650 and 652 engage each other. In some embodiments the connecting member 660 would allow for a reversible bond between the conduit 640 and the connector 601. In some embodiments the connector 601 is configured to have raised ridges (not depicted). In some embodiments the connecting member 660 may be configured with engaging snaps (not depicted). In some embodiments the connecting member 660 does not extend the entire length of the connector 601. In some embodiments the conduit 640 does not have a collar 658 (depicted in FIG. 6A).

Figure 7:
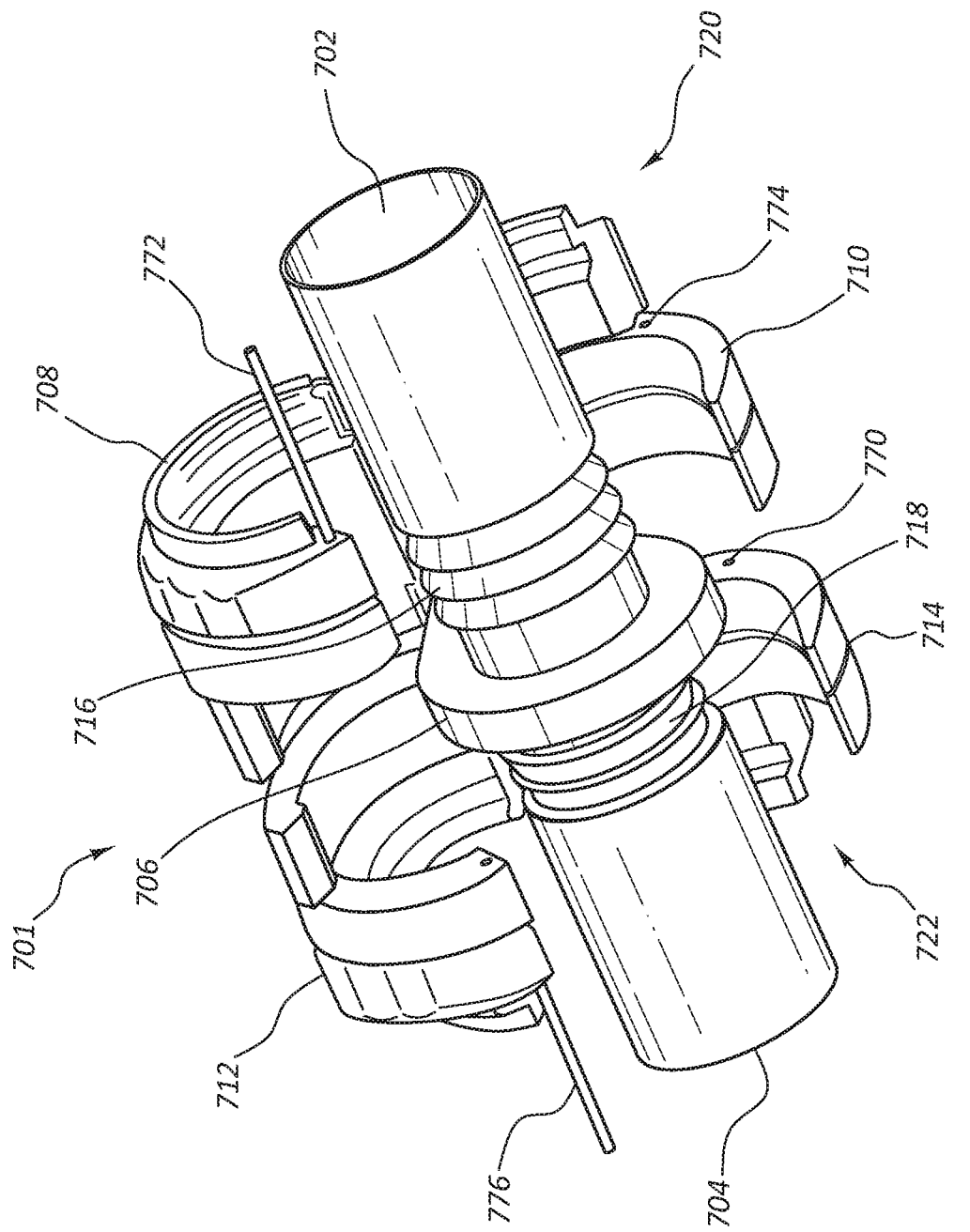
FIG. 7 is a simplified perspective view of certain components of a vascular access system.

FIG. 7 depicts a connector 701 which can be used in a vascular access system 700 (not depicted in full) to couple two conduits (not shown) to either a first end 702 or a second end 704 of the connector 701. The connector 701 can take any suitable form, and in some embodiments is configured to be implanted subcutaneously within a human. The connector 701 may be implanted subcutaneously and extravascularly. The connector 701 may be configured to improve or maximize laminar flow through the lumen, and to minimize or eliminate potential turbulent flow through the system, more specifically blood passing through the system. The connector 701 may be configured to join a first artificial conduit with a first outside diameter to a second artificial conduit with a second outside diameter in such a way that there is a continuous lumen between the two conduits. In an alternative embodiment the first artificial conduit and the second artificial conduit have the same outside diameter. In some embodiments the connector 701 is capable of joining a single artificial conduit.

In some embodiments the connector 701 comprises the first end 702 with an outside diameter configured to engage with a first end of an artificial conduit. The connector 701 may further comprise the second end 704 and a flange 706. In some embodiments, the flange 706 comprises holes (not shown) through which grasping tools or suture may be passed. In some embodiments, the connector 701 may comprise connecting members 720 and 722. In some embodiments, the connecting member 720 may comprise a first securing device 708 pivotably coupled with the flange 706 and a second securing device 710 pivotably couple with the flange 706, such that the two securing devices 708 and 710 are configured to close over the first end 702 of the connector to securely fasten at least one conduit to the connector 701. Connecting member 722 may comprise two securing devices 712 and 714 which are configured to close over the second end 704 of the connector 701. In some embodiments there is no taper from the first end 702 of the connector 701 to the second end 704; instead, the inside diameter of the lumen remains constant throughout the length of the connector 701.

In some embodiments the connector 701 comprises ridges 716 and 718 on the body of the connector closest to the flange 706. These ridges 716 and 718 are configured to more securely hold the conduit when an end user slides it onto the first end 702 or the second end 704 of the connector 701. In one embodiment, the first connecting member 720 and the second connecting member 722 are configured to close over at least one conduit once the end user slides it over first end 702 or the second end 704 of the connector 701, and are configured to compress the conduit against ridges 716 or 718 respectively, to create more engagement with the connector 701. In some embodiments the end user can continue to push the conduit past the ridges 716 and/or 718 until the conduit abuts against the flange 706. The end user can then close the securing devices 708 and 710 to compressibly engage the conduit and secure it to the connector 701.

In some embodiments the securing devices 708 and 710 of connecting member 720 are configured with a key 772 that an end user can engage with keyhole 774 to lock the securing devices 708 and 710 together. In some embodiments the securing devices 712 and 714 of connecting member 722 are configured with a key 776 that an end user can engage with keyhole 770 to lock the securing devices 712 and 714 together. In some embodiments the keys 772 and 776 lock irreversibly with keyholes 774 and 770 respectively. In some embodiments the keys 772 and 776 lock reversibly with keyholes 774 and 770 respectively.

Figure 8:
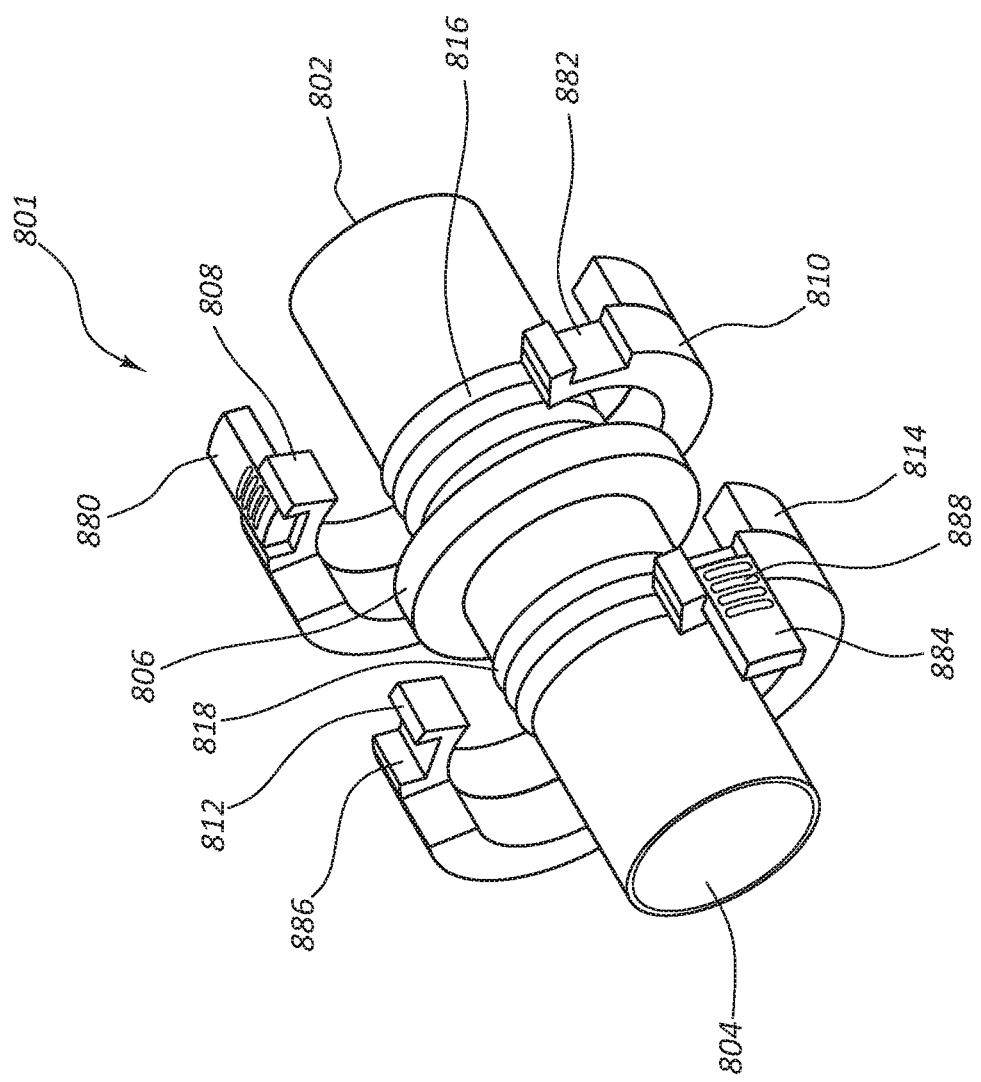
FIG. 8 is a simplified perspective view of certain components of a vascular access system.

FIG. 8 depicts connector 801 in which keys 884 and 880 engage keyhole grooves 886 and 882 respectively. In some embodiments the end user can slide the keys 884 and 880 to engage keyhole grooves 886 and 882 once the securing devices, such as 808 and 810, have been closed over a conduit and a first end 802 of the connector 801. In some embodiments the key irreversibly engages the keyhole. In some embodiments the key reversibly engages the keyhole. In some embodiments the keys 884 and/or 880 can be configured with ridges 888 to provide additional friction grip for an end user sliding the key into the keyhole. Analogous to other embodiments discussed above, FIG. 8 also comprises: securing devices 812 and 814; connector second end 804; flange 806; and ridges 818 and 816.

Figure 9:
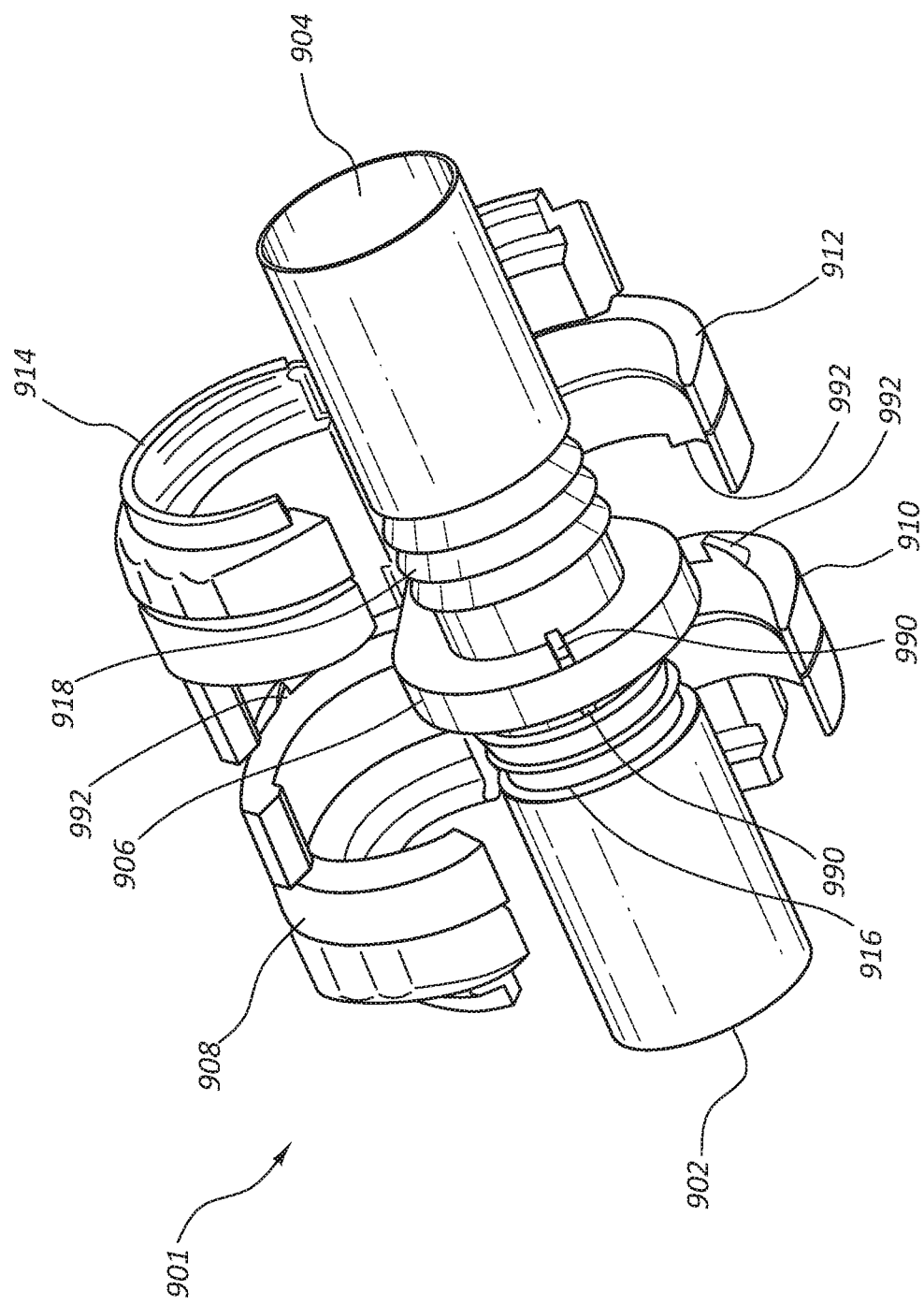
FIG. 9 is a simplified perspective view of certain components of a vascular access system.

FIG. 9 depicts a connector 901 in which the securing devices, such as 908 and 910, have member interfits 992 which can reversibly or irreversibly engage with flange interfits 990 on a flange 906. In some embodiments the flange 906 is split down the middle and is configured to twist with respect to the other side of the flange 906 so that the flange interfits 990 can be twisted to engage member interfits 992 on the securing devices 908 and 910. Analogous to other embodiments discussed above, FIG. 9 also comprises: securing devices 912 and 914; connector first end 902 and second end 904; and ridges 918 and 916.

Figure 10:
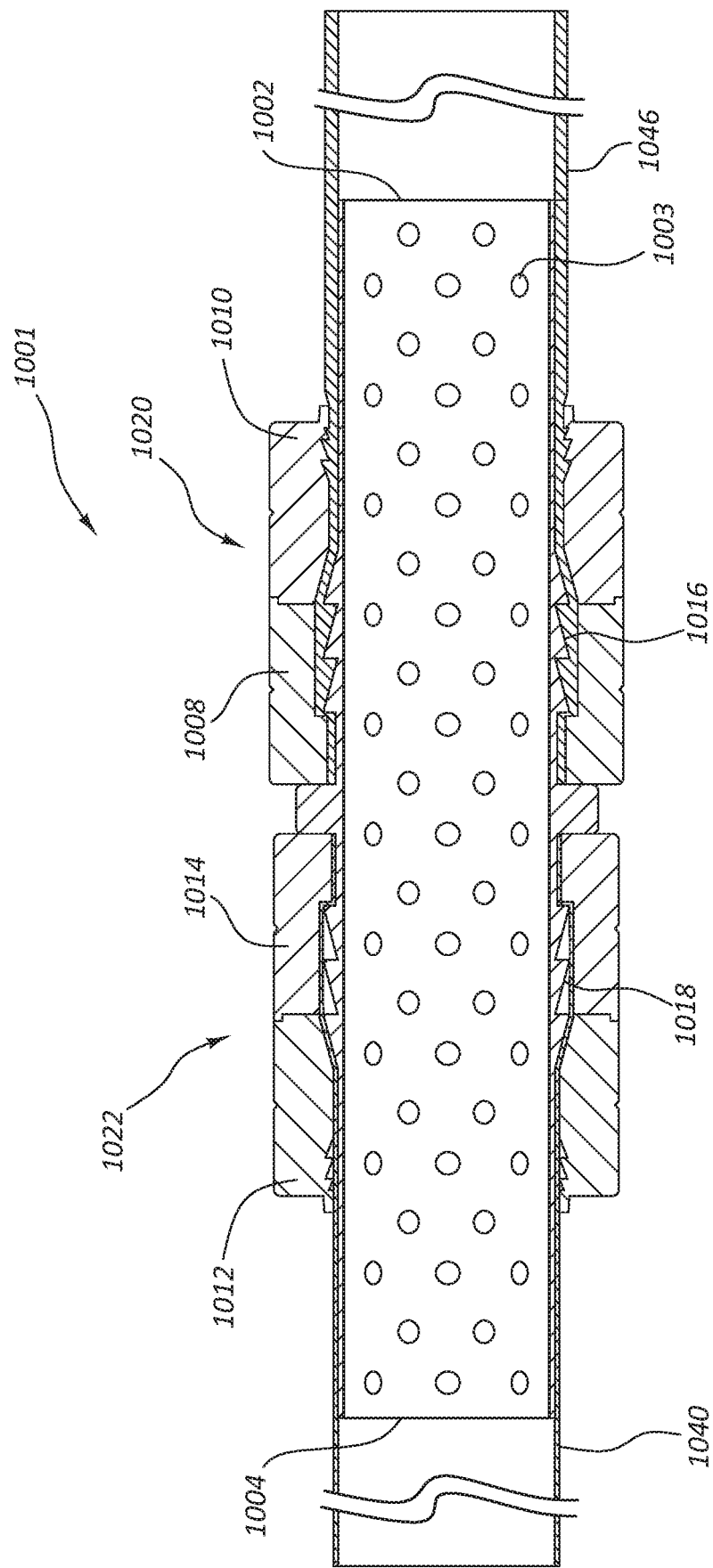
FIG. 10 is a simplified cross-section view of certain components of a vascular access system.

FIGS. 10-14 illustrate various geometries of the inside layer of the luminal wall of any one of the connectors discussed in this disclosure. FIG. 10 illustrates a cross section of a connector 1001 configured with two connecting members 1020 and 1022 to couple conduits 1040 and 1046. In some embodiments the inside lumen has a series of dimples 1003 spaced as depicted in FIG. 10. These dimples 1003 may improve laminar flow through the lumen of the connector 1001. Analogous to other embodiments discussed above, FIG. 10 also comprises: securing devices 1008, 1010, 1012 and 1014; connector first end 1002 and second end 1004; conduits 1040 and 1046; and ridges 1018 and 1016.

Figure 11:
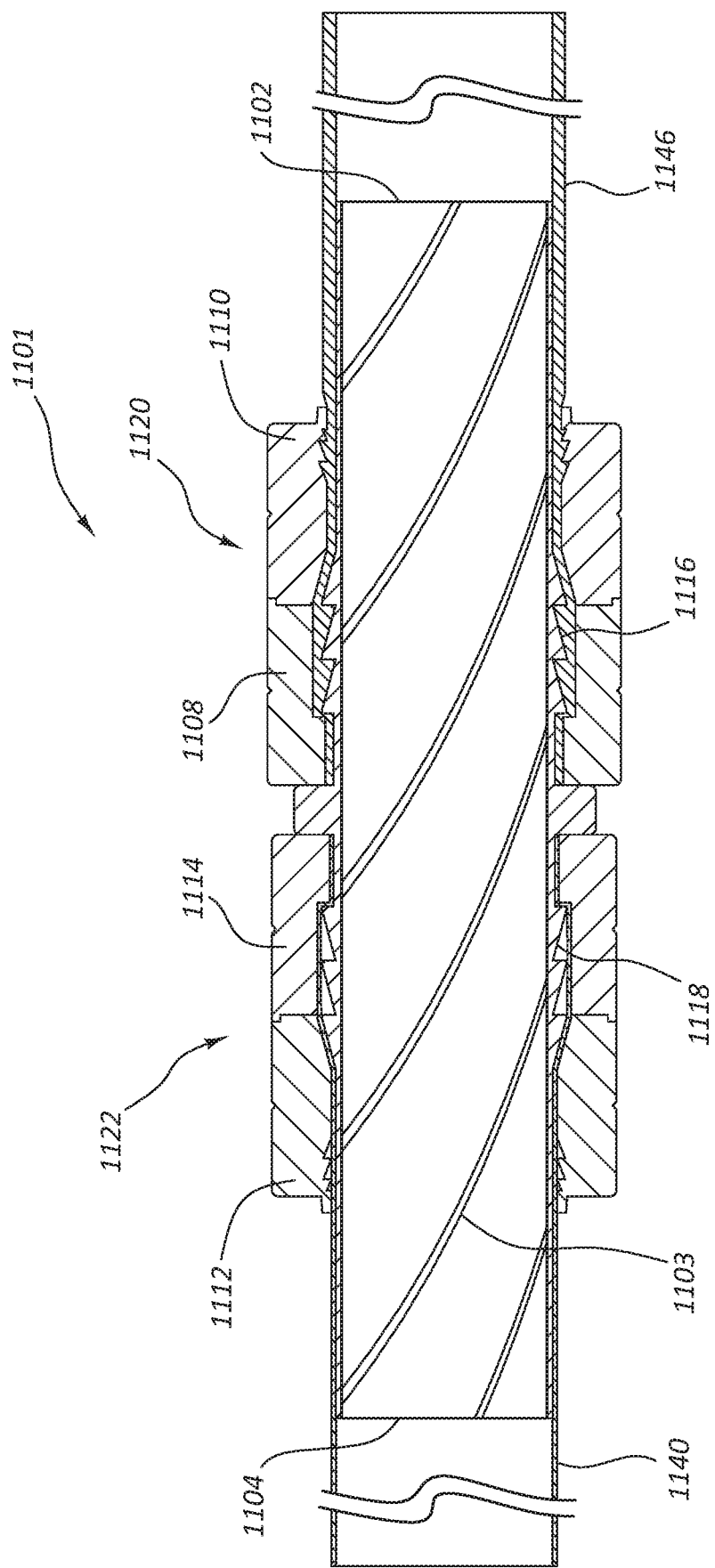
FIG. 11 is a simplified cross-section view of certain components of a vascular access system.

FIG. 11 depicts connector 1101 in which the luminal wall of the connector 1101 is configured with ridges 1103 configured in a spiral along the length of the connector 1101.

This spiraling of the ridges 1103 may enhance laminar flow through the lumen of the connector 1101. Analogous to other embodiments discussed above, FIG. 11 also comprises: connecting members 1120 and 1122; securing devices 1108, 1110, 1112 and 1114; connector first end 1102 and second end 1104; conduits 1140 and 1146; and ridges 1118 and 1116.

Figure 12:
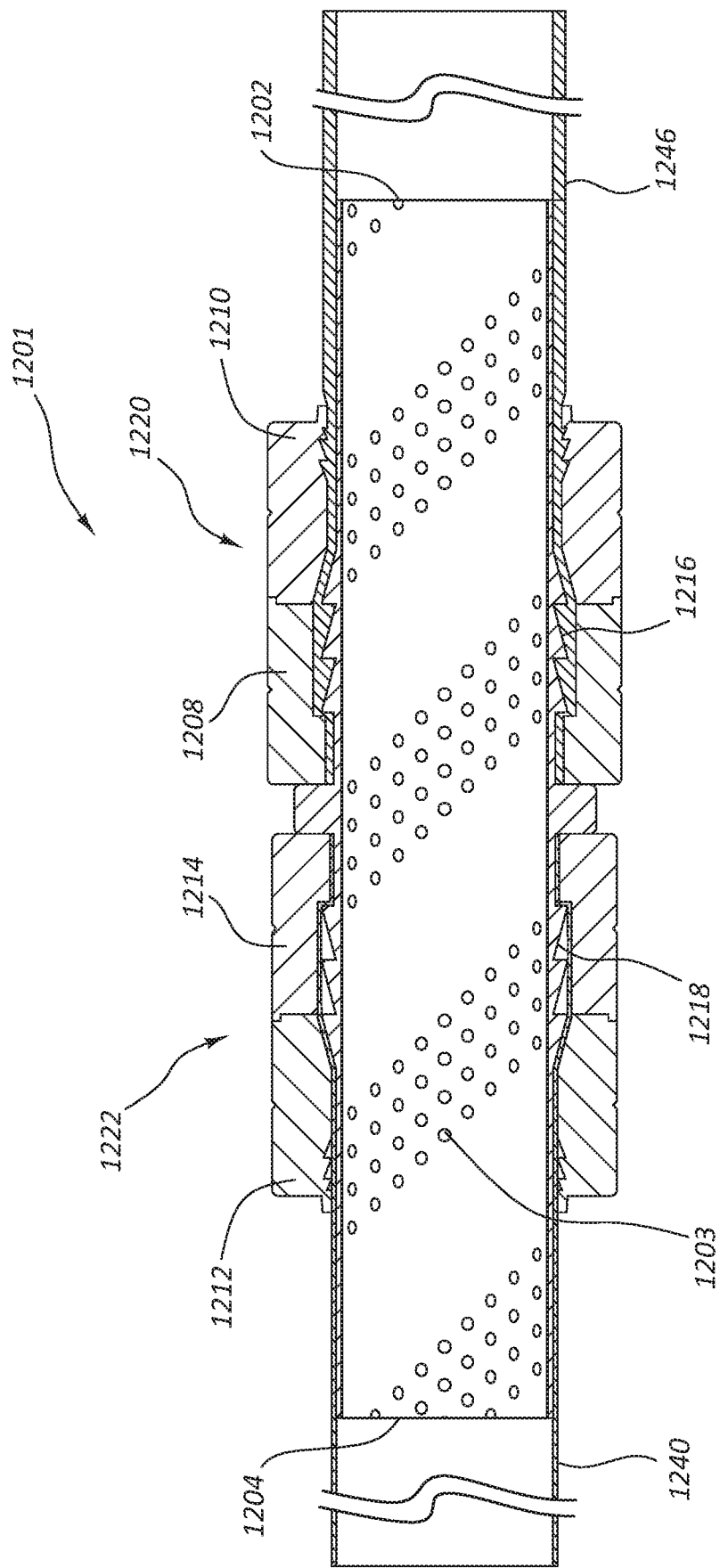
FIG. 12 is a simplified cross-section view of certain components of a vascular access system.

FIG. 12 depicts connector 1201 in which the luminal wall is configured with dimpling or raised bumps 1203 in a configuration as depicted. The spiraling of the dimpling 1203 may enhance laminar flow through the lumen of the connector 1201. Analogous to other embodiments discussed above, FIG. 12 also comprises: connecting members 1220 and 1222; securing devices 1208, 1210, 1212 and 1214; connector first end 1202 and second end 1204; conduits 1240 and 1246; and ridges 1218 and 1216.

Figure 13A:
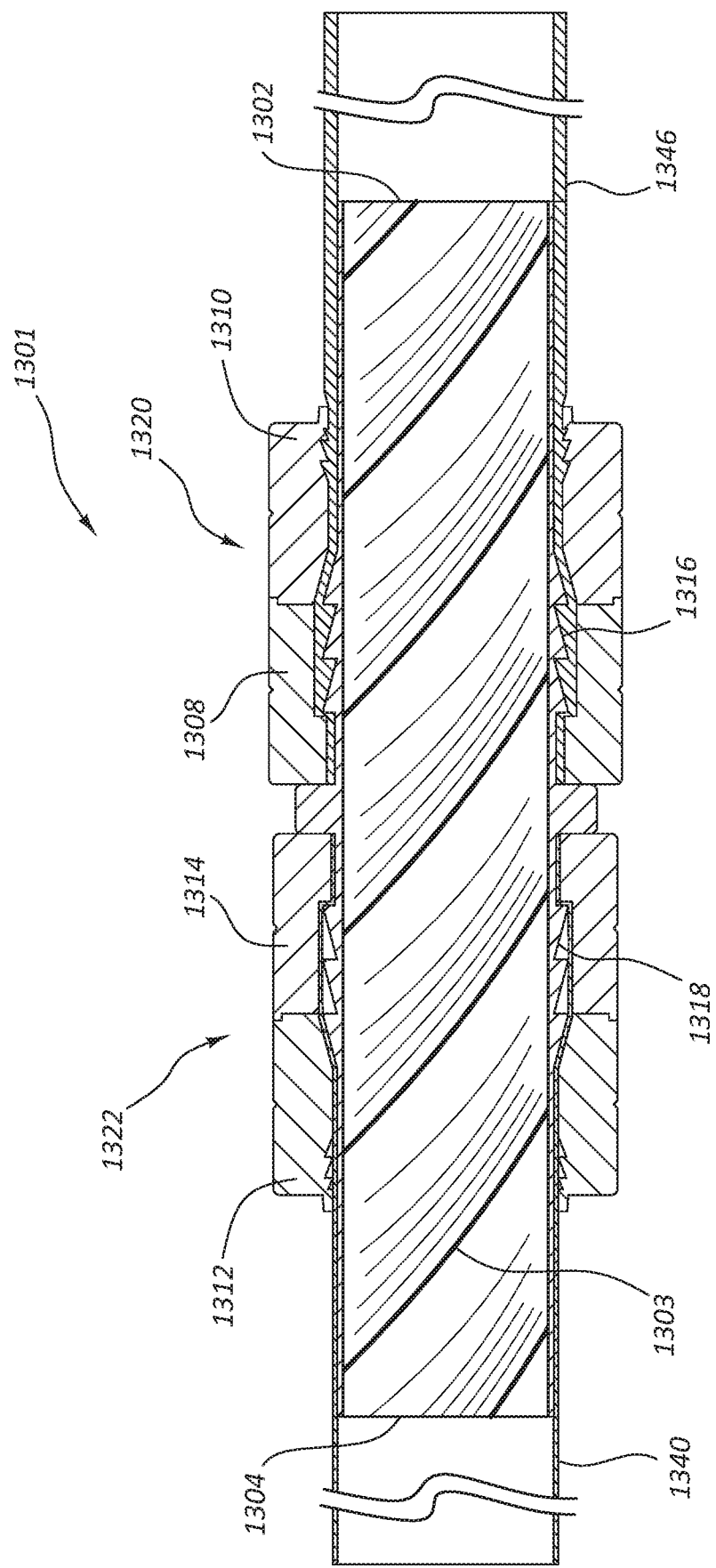
FIG. 13A is a simplified cross-section view of certain components of a vascular access system.

FIG. 13A depicts connector 1301 in which the luminal wall is configured with a spiral lumen 1303. The spiral lumen 1303 may enhance laminar flow through the lumen of the connector 1301. Analogous to other embodiments discussed above, FIG. 13A also comprises: connecting members 1320 and 1322; securing devices 1308, 1310, 1312 and 1314; connector first end 1302 and second end 1304; conduits 1340 and 1346; and ridges 1318 and 1316.

Figure 13C:
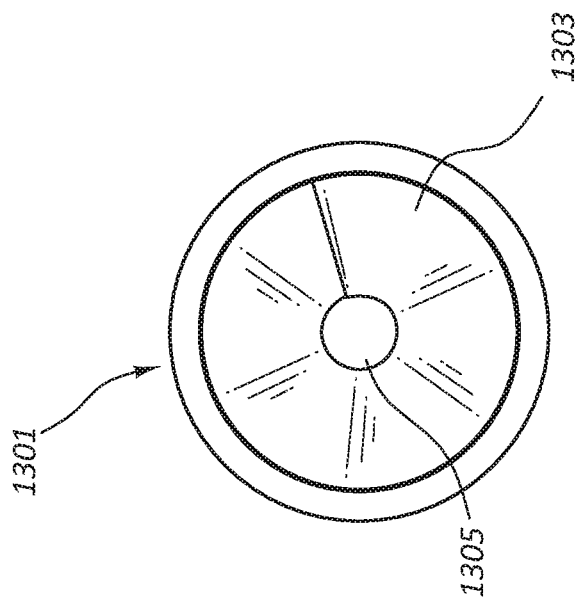
FIG. 13C is a simplified orthogonal view of certain components of the vascular access system of FIG. 13A.
Figure 13B:
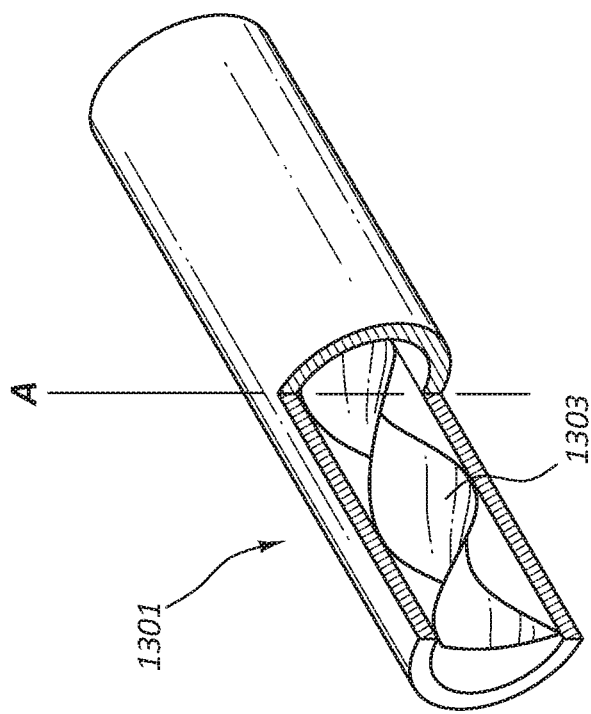
FIG. 13B is a partial simplified cut-away view of certain components of the vascular access system of FIG. 13A.

FIG. 13B depicts a cut-away of portions of the connector 1301 to better visualize the spiral lumen 1303 running the length of the connector 1301.

FIG. 13C depicts a cross-section along line A from FIG. 13B showing the spiral lumen 1303. As can be visualized in FIG. 13C there is a smaller inner lumen 1305 that runs along the inside of the spiral lumen 1303.

Figure 14:
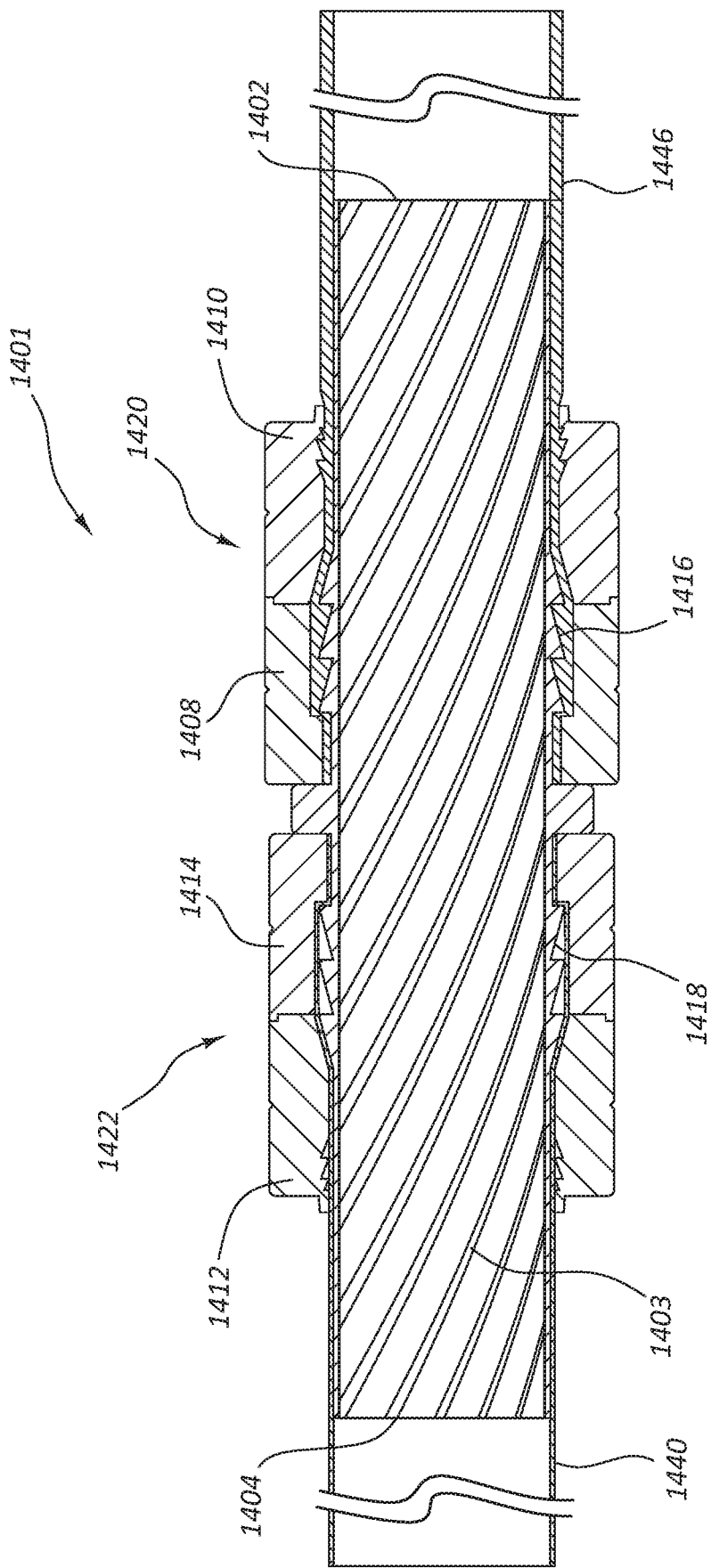
FIG. 14 is a simplified cross-section view of certain components of a vascular access system.

FIG. 14 depicts connector 1401 in which the luminal wall of the connector 1401 is configured with grooves 1403 configured in a spiral along the length of the connector 1401. This spiraling of the grooves 1403 may enhance laminar flow through the lumen of the connector 1401. Analogous to other embodiments discussed above, FIG. 14 also comprises: connecting members 1420 and 1422; securing devices 1408, 1410, 1412 and 1414; connector first end 1402 and second end 1404; conduits 1440 and 1446; and ridges 1418 and 1416.

Figure 15A:
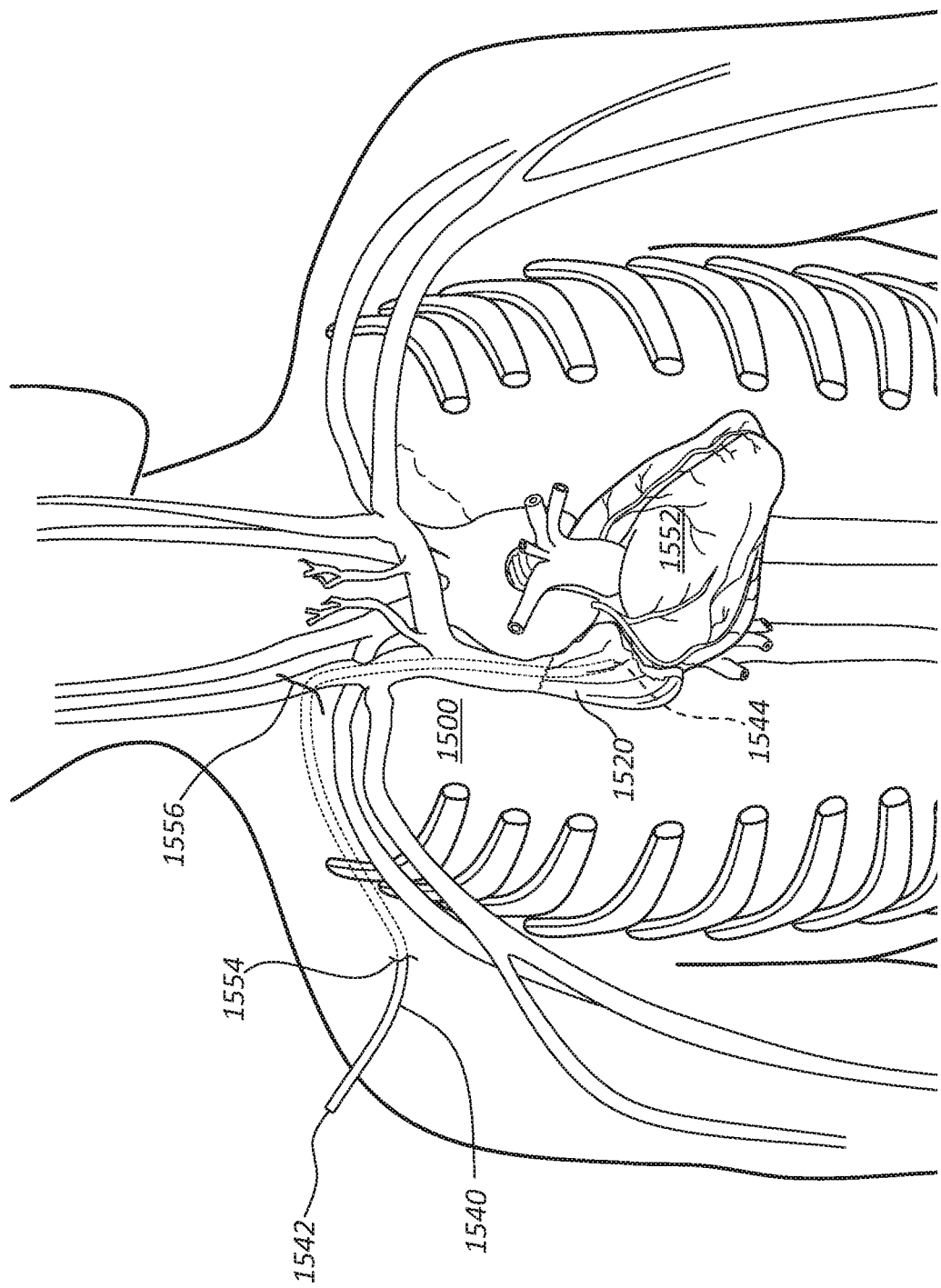
FIG. 15A depicts certain components of a vascular access system that has been inserted into a patient.

FIG. 15A depicts one embodiment for the deployment of a first tubular conduit 1540 inside the body and vasculature of a patient 1500. As shown in FIG. 15A, such a medical procedure may initially involve making a first incision 1556 in or adjacent to the neck of the patient 1500 to access the internal jugular vein of the patient 1500. A guidewire (not depicted) may then be passed into the internal jugular vein to the inferior vena cava, followed by a dilator (not depicted) that is passed over the guidewire to facilitate insertion of an introducer. The dilator may then be removed, and the introducer (not depicted) passed over the guidewire into the internal jugular vein of the patient 1500. Once the introducer is placed within the internal jugular vein, a first end 1544 of the first conduit 1540 may be inserted through the introducer and advanced within the patient 1500 such that the first end 1544 of the first conduit 1540 passes through the superior vena cava 1560 (depicted in FIG. 15B) into the right atrium of a heart 1552 as depicted in FIGS. 15A-15D. Advancement of the first conduit 1540 into the patient 1500 may be done under fluoroscopic guidance.

After the first end 1544 of the first conduit 1540 passes through the superior vena cava 1560 and has been placed within the right atrium 1558 (depicted in FIB. 15B) of the heart 1552, a second incision 1554 may be made in the shoulder region of the patient 1500 (e.g., adjacent the deltopectoral groove). A tunneling device may then be used to establish a subcutaneous path between the first incision 1556 in the neck region of the patient 1500 and the second incision 1554 in the shoulder region of the patient 1500. A second end 1542 of the first conduit 1540 may then be inserted into the first incision 1556 and advanced along the path established by the tunneling device (i.e., the first conduit 1540 is tunneled) such that the first conduit 1540 extends from the right atrium of the heart 1552 to the second incision 1554 in the shoulder region of the patient 1500 as shown in FIG. 15A. As depicted in FIG. 15B, the superior vena cava 1560 and inferior vena cava 1562 empty into the right atrium 1558 of the heart 1552.

Once the first end 1544 of the first conduit 1540 has been placed such that the first conduit 1540 extends from the right atrium 1558 of the heart 1552 past the first incision 1556 to the second incision 1554 in the shoulder region of the patient 1500, a third incision 1564 (see FIG. 15C) may be made in the arm of the patient 1500 adjacent the target site of, for example, an arteriovenous graft. For example, the third incision 1564 may be made at a position that is upstream of, for example, an occlusion or failure in the arteriovenous graft. A second end 1534 of a second tubular conduit 1546 may then be coupled to the arteriovenous graft adjacent the third incision 1564 in the arm of the patient 1500 (see FIGS. 15A-15D). For example, in some embodiments, the arteriovenous graft may be pierced adjacent the third incision 1564 by a needle. A guidewire (not depicted) may then be inserted through the needle and into the arteriovenous graft of the patient 1500. In some embodiments the second end 1534 of the second conduit 1546 is, for example, anastomosed to the arteriovenous graft, or any other vasculature in the arm of the patient 1500.

Figure 15C:
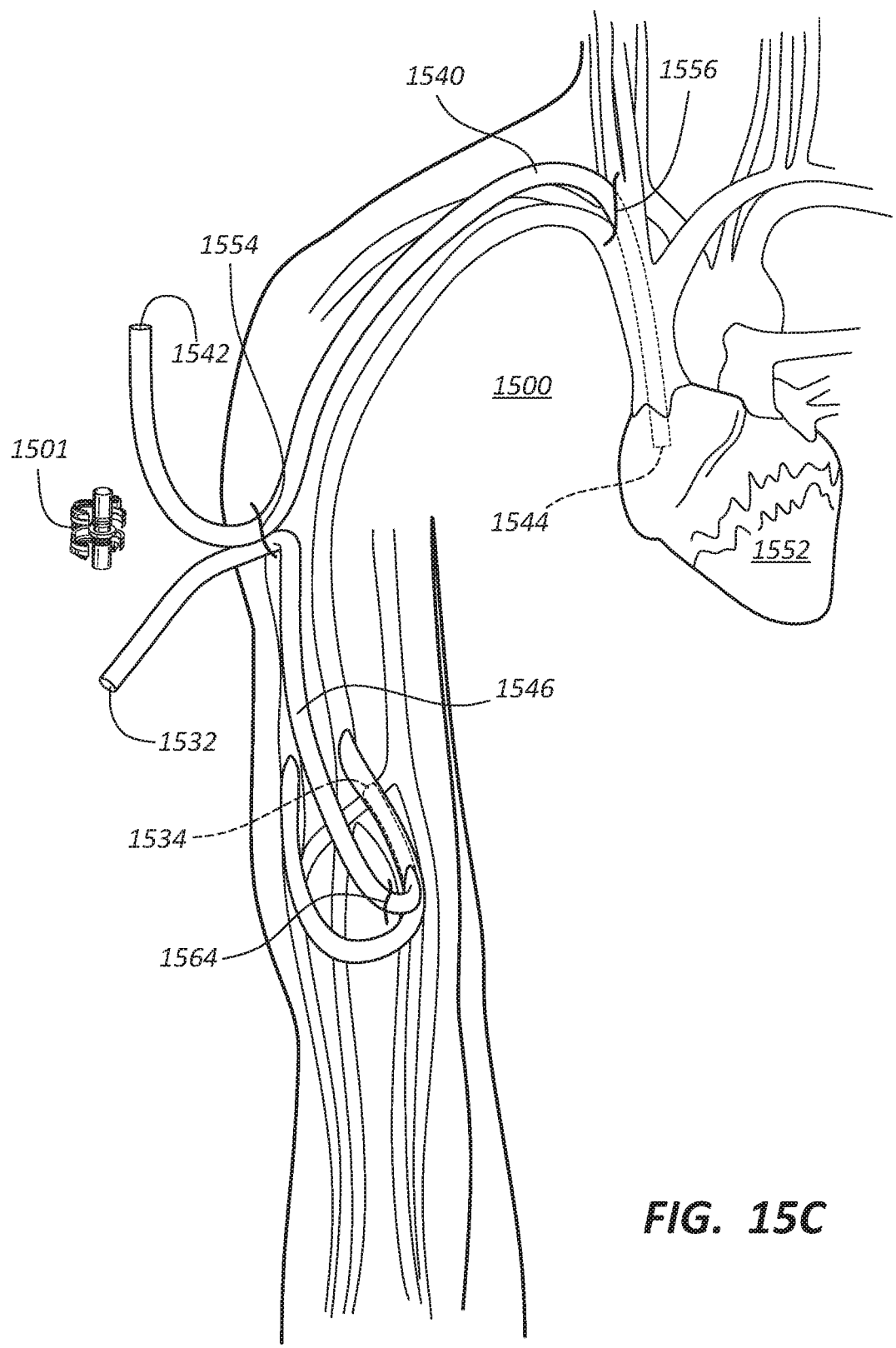
FIG. 15C depicts certain components of the vascular access system of FIG. 15A positioned in the patient.

A tunneling device (not depicted) may then be used to establish a subcutaneous path between the third incision 1564 in the arm of the patient 1500 to the second incision 1554 in the shoulder region of the patient 1500 (see FIG. 15C). The second conduit 1546 may then be inserted into and advanced through the tunneling device such that the first end 1532 of the second conduit 1546 extends from the third incision 1564 to the second incision 1554. The tunneling device (not depicted) may then be removed such that the second conduit 1546 is disposed within the patient 1500 as shown in FIG. 15C. In this manner, the tunneling device may facilitate placement and delivery of the second conduit 1546 within the patient 1500.

With the first end 1544 of the first conduit 1540 disposed within the right atrium of the heart 1552 of the patient 1500, the second end 1542 of the first conduit 1540 may then, if needed, be cut to the appropriate length. In other words, the first conduit 1540 may initially (e.g., when manufactured and inserted as described above) have a length that is longer than is needed to establish a flow path from the right atrium of the heart 1552 of the patient 1500 to the second incision 1554 in the shoulder region of the patient 1500. The first conduit 1540 may then be cut to proper length to facilitate coupling of the second conduit 1546 to the first conduit 1540 at the second incision 1554 in the shoulder region of the patient 1500.

Similarly, in some embodiments, the second conduit 1546 has an initial length that is longer than is needed to establish a flow path from the second incision 1554 in the shoulder region of the patient 1500 to the third incision 1564 in the arm of the patient 1500. In such embodiments, the first end 1532 of the second conduit 1546 may be cut to the appropriate length once the second conduit 1546 has been inserted into the patient 1500. In other embodiments, no cutting of the second conduit 1546 is needed.

Once the first conduit 1540 and the second conduit 1546 are the proper length, the second conduit 1546 may be coupled to the first conduit 1540 by the connector 1501. The connector 1501 will secure both conduits in such a way as to establish a fluid-tight connection between the first conduit 1540 and the second conduit 1546. Establishment of a fluid-tight connection can be confirmed by attaching the second end 1532 of the second conduit 1546 to a syringe and advancing fluid (e.g., heparinized saline) through the system.

Figure 15D:
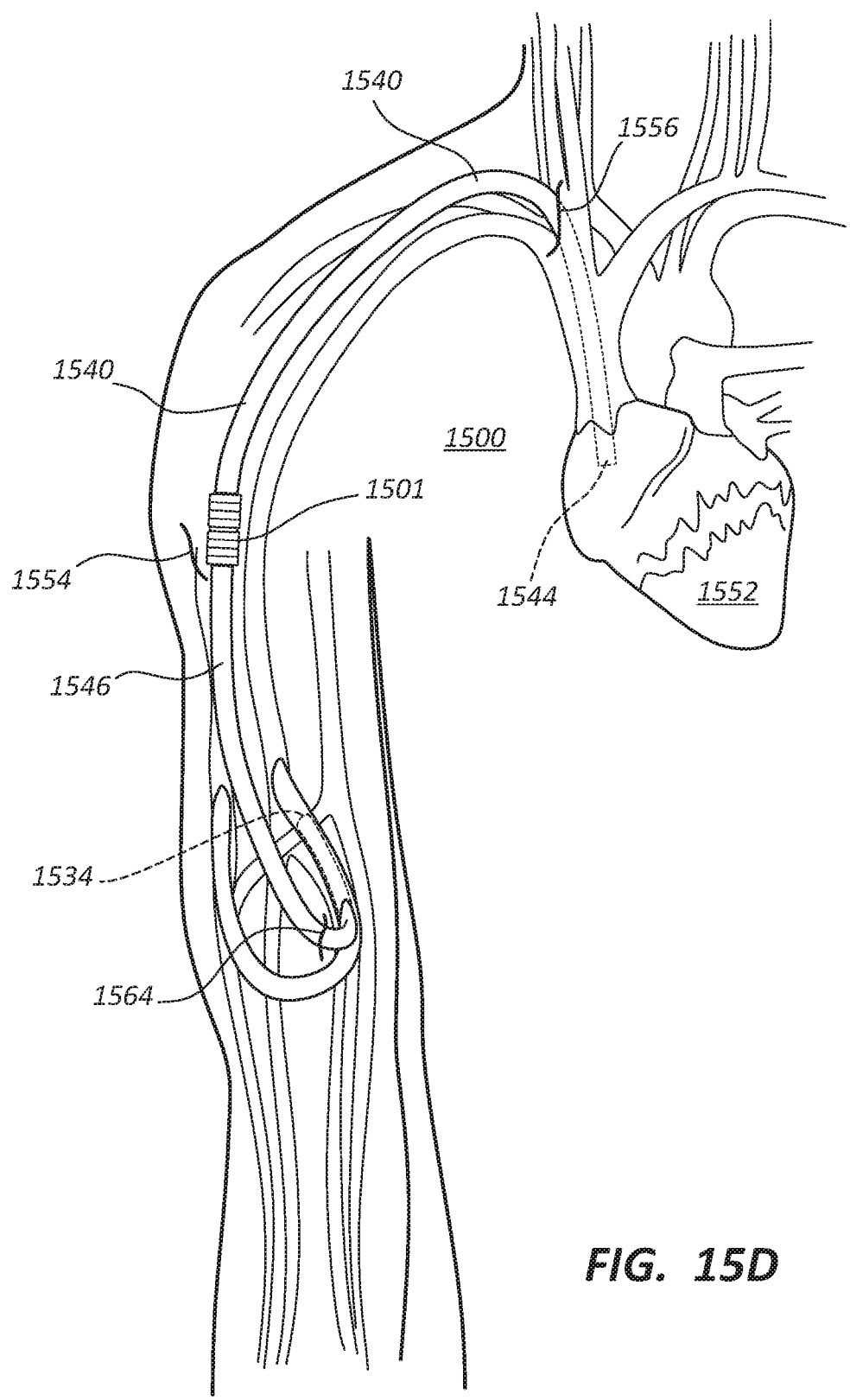
FIG. 15D depicts certain components of the vascular access system of FIG. 15A positioned in the patient.

Once a flow path from, for example, the arteriovenous graft to the heart 1552 has been established in patient 1500 as shown in FIG. 15D, the first incision 1556, the second incision 1554, and the third incision 1564 may be closed via any suitable technique. In this manner, the vascular access system may, when implanted and assembled, be a fully subcutaneous surgical implant. The implanted and assembled vascular access system may also, as described above, be implanted without establishing a venous anastomosis. Analogous to other embodiments discussed above, FIG. 15D also comprises: a first end 1544 of conduit 1540; a second end 1534 of a second tubular conduit 1546; and connector 1501 in a closed configuration.

The implanted vascular access system may be used to facilitate vascular access. For example, in the case of hemodialysis, a practitioner may insert a first needle through the skin of the patient 1500 and into the vascular access system. More particularly, the first needle may be inserted into the second conduit 1546. Fluid may be withdrawn from the vascular access system and drawn into a dialysis machine that purifies the blood. The purified blood may then be returned to the patient 1500 via a second needle that extends through the skin of the patient 1500 and into a more central location of the second conduit 1546.

In an alternative embodiment, the implanted vascular access system may be used to improve, prevent, or correct peripheral arterial disease (PAD). The steps of the procedure would be similar to those described above but would require shunting blood across a stenosed region of a vessel to another vessel to improve blood flow to the extremities.

Figure 16:
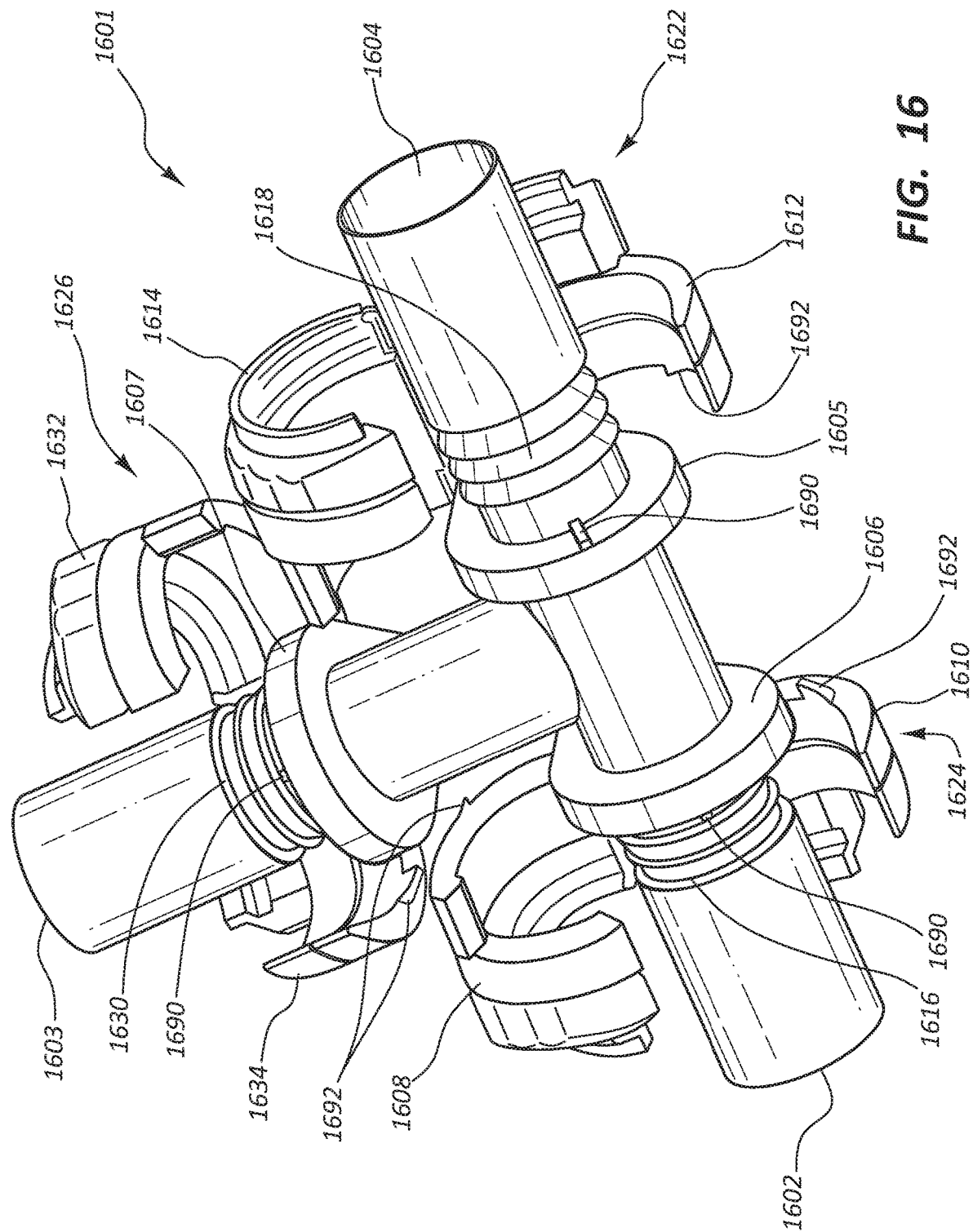
FIG. 16 is a simplified perspective view of certain components of a vascular access system.

FIG. 16 is another embodiment of a connector 1601. In the embodiment of FIG. 16, the vascular access system may comprise a T or Y shaped branched connector 1601. A T or Y shaped connector may releasably connect to three conduits. In other embodiments, the connector 1601 may releasably connect to more than three conduits. This type of connector 1601 could also be used to connect multiple grafts or catheters at one of three ends 1602, 1603, and 1604. In this embodiment the end user could create a fluid connection between three different vessels. In alternative embodiments each of these three ends could be further divided so that each end could attach one or more conduits to the connector and thus create a fluid connection between multiple vessels in the body. This connector 1601 may be utilized in a debranching procedure of the aorta, as it provides a quick connection between multiple different conduits which may be anastomosed to multiple vessels. A debranching procedure is often performed when an aneurysm or other pathology necessitates bypass of a section of the aorta with multiple large arterial branches, such as the renal or mesenteric arteries. The physician will bypass the entire segment of the aorta and create multiple bypass grafts leading to the end organs that are normally fed by this segment of the aorta. In this manner a connector like 1601 can provide additional manners of connecting artificial conduits with vessels, and provide a way for the end user to attach and detach these conduits to the vessels.

As is depicted in FIG. 16, the third end 1603 of the connector 1601 which is configured to have ridges 1630 to provide a friction bond with a conduit. In some embodiments this third end 1603 comprises a connecting member 1626 which may comprise a first securing device 1632 pivotably coupled with a flange 1607 and a second securing device 1634 pivotably coupled to flange 1607. In this way securing devices 1632 and 1634 are configured to close over a third end 1603 of the connector 1601 to securely fasten at least one conduit to the connector. The depicted embodiment also illustrates the connector 1601 with member interfits 1692 and flange interfits 1690 which function as described in the description of FIG. 9. Member interfits 1692 are configured to reversibly or irreversibly engage with the corresponding flange interfits 1690. Connector 1601 may also lack the member interfits 1692 and flange interfits 1690. In the depicted embodiment, the branched connector 1601 is T-shaped, however, in other embodiments, the branched connector may be of any other branched shape (e.g., Y-shaped). It is also contemplated that the branched connector may have more than three ends, all in fluid connection with each other. Analogous to other embodiments discussed above, FIG. 16 also comprises: connecting members 1622 and 1624; securing devices 1608, 1610, 1612 and 1614; ridges 1618 and 1616; and flanges 1605 and 1606.

The steps of the procedure described above are only exemplary in nature. In other words, the vascular access system may be implanted into the patient 1500 via a procedure that deviates somewhat from the procedure described above. One of ordinary skill in the art, having the benefit of this disclosure, will also appreciate that some of the steps described above need not be performed in the precise order that is specified above.

During placement and/or implantation of vascular access system, such as those describe above, various strategies may be employed to reduce or prevent the loss of blood. For example, in some embodiments, various clamps are used during implantation to restrict fluid flow through a portion of the first conduit and/or the second conduit. In other or further embodiments, the first conduit and/or the second conduit include one of more valves that obstruct fluid flow, thereby preventing the loss of blood during implantation. For example, in some embodiments, a valve is disposed adjacent the second end of the first conduit or the first end of the second conduit. The valve may be configured to transition from a first configuration that prevents fluid flow through the valve when the first conduit and the second conduit are uncoupled from each other to a second configuration that allows fluid flow through the valve when the first conduit and the second conduit are coupled to each other. In some embodiments, fluid flow is restricted by a balloon that is disposed within a portion of the vascular access assembly.

Kits that include a vascular access assembly are also within the scope of this disclosure. For example, a kit may include any of the vascular access system described above. The kit may also include other elements, such as instructions for using the vascular access system to establish a flow path from an artery or an arteriovenous graft of a patient to a heart of the patient. Kits may additionally or alternatively include (1) one or more clamps for preventing fluid flow through a portion of a tubular conduit, (2) scissors, (3) plugs for preventing fluid flow through an end of a tubular conduit, (4) a tunneling device, (5) a syringe, (6) one or more guidewires, (7) gauze pads, (8) contrast fluid, and/or (9) saline (e.g., heparinized saline), among other potential elements.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

While the disclosure is susceptible to various modifications and implementation in alternative forms, specific embodiments have been shown by way of non-limiting example in the drawings and have been described in detail herein. However, it should be understood that the invention is not intended to be limited to the particular forms disclosed. Rather, the invention includes all modifications, equivalents, and alternatives falling within the scope of the invention as defined by the following appended claims and their legal equivalents.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

We claim:

1. A vascular access system, comprising:
   a first conduit;
   a second conduit; and
   a connector comprising an inside luminal wall, a first end, a second end, a first connecting member on the first end, and a second connecting member on the second end,
   the connector being configured to couple to an end of the first conduit and to an end of the second conduit such that there is a continuous lumen from the first conduit to the second conduit, wherein the connector is configured to irreversibly couple to at least one of the first conduit and the second conduit,
   wherein both the first and second connecting members further comprise a hinge,
   wherein the connector comprises a flange disposed between the first end and the second end,
   wherein the connector comprises a first circumferential ridge disposed on the first end adjacent the flange and a second circumferential ridge disposed on the second end adjacent the flange,
   wherein each of the first and second circumferential ridges comprise a shoulder facing toward the flange,
   wherein the first connecting member and the second connecting member each comprise a radially inwardly extending protrusion adjacent to the flange and comprising a shoulder facing away from the flange,
   wherein at least a portion of the first conduit is disposed between the shoulder of the first circumferential ridge and the shoulder of the inwardly extending protrusion of the first connecting member when the first connecting member compresses the first conduit against the first end of the connector, and
   wherein at least a portion of the second conduit is disposed between the shoulder of the inwardly extending protrusion of the second circumferential ridge and the shoulder of the second connecting member when the second connecting member compresses the second conduit against the second end of the connector.

2. The vascular access system of claim 1, wherein the first and/or second conduits are configured with an impermeable wall segment in a portion nearest to the connector.

3. The vascular access system of claim 1, wherein the first and/or second conduits are configured with an elastomeric wall segment to reduce bleeding after puncture or to improve sealing of the connector.

4. The vascular access system of claim 1, further comprising a first therapeutic agent and a second therapeutic agent that are associated with one or both of an inner luminal surface and an outer abluminal surface of any of the first conduit, the second conduit, or the connector, wherein the vascular access system is configured to deliver a therapeutically effective dose of the first therapeutic agent and/or the second therapeutic agent to a mammal when the vascular access system is implanted within the mammal.

5. The vascular access system of claim 1, wherein the first connecting member or the second connecting member further comprises at least one of snap fits, interfits, teeth, threaded connectors, key system, tension clips, seals, friction ridges, or any combination thereof.

6. The vascular access system of claim 1, wherein the inside luminal wall of the connector is configured with a coating layer.

7. The vascular access system of claim 1, wherein the first and/or second connecting members comprise at least one ridge that spans at least a portion of an exterior circumference of the connector.

8. The vascular access system of claim 7, wherein the first connecting member further comprises securing devices and the second connecting member further comprises securing devices, and wherein the securing devices are configured to compress at least one of said conduits against said at least one ridge.

9. The vascular access system of claim 1, wherein the first connecting member and the second connecting member are each configured to couple with multiple artificial conduits of varying outside diameter, such that coupling of one of the first connecting member and the second connecting member with an artificial conduit forms a fluid tight lumen between the artificial conduit and the connector, wherein the first conduit has a first outside diameter, wherein the second conduit has a second outside diameter, and wherein the second outside diameter is different from the first outside diameter.

10. The vascular access system of claim 1, wherein the inside luminal wall of the connector comprises ridges that spiral along a length of the connector that are configured to enhance laminar flow.

11. The vascular access system of claim 1, wherein the connector is irreversibly coupled to the first conduit and the second conduit.

12. A vascular access system, comprising:
a first conduit having a first outside diameter;
a second conduit having a second outside diameter, wherein the second outside diameter is different from the first outside diameter; and
a connector comprising an inside luminal wall, a first end, a second end, a first connecting member on the first end, and a second connecting member on the second end,
wherein the first connecting member and the second connecting member are each configured to couple with multiple artificial conduits of varying outside diameter, such that coupling of one of the first connecting member and the second connecting member with an artificial conduit forms a fluid-tight lumen between the artificial conduit and the connector,
wherein the connector being configured to couple to an end of the first conduit and to an end of the second conduit such that there is a continuous lumen from the first conduit to the second conduit,
wherein the first connecting member comprises a first set of securing devices and the second connecting member comprises a second set of securing devices,
wherein at least one of the first set of securing devices and the second set of securing devices is configured to compress at least one of the first conduit and the second conduit against at least one of the first end and the second end of the connector,
wherein the first set of securing devices and the second set of securing devices each comprise engaging teeth,
wherein when the at least one of the first set of securing devices and the second set of securing devices compresses the at least one of the first conduit and the second conduit against the at least one of the first end and the second end, some of the engaging teeth engage with one another and some of the engaging teeth remain unengaged wherein the connector comprises a flange disposed between the first end and the second end,
wherein the first end and the second end of the connector each comprise a circumferential ridge disposed adjacent the flange wherein each of the circumferential ridges comprise a shoulder oriented toward the flange,
wherein the first set of securing devices and the second set of securing devices each comprise a radially inwardly extending protrusion between the engaging teeth and the flange, comprising a shoulder oriented away from the flange,
wherein at least a portion of the first conduit is disposed between the shoulder of the circumferential ridge of the first end of the connector and the shoulder of the first set of securing devices when the first set of securing devices compresses the first conduit against the first end of the connector, and
wherein at least a portion of the second conduit is disposed between the shoulder of the circumferential ridge of the second end of the connector and the shoulder of the second set of securing devices when the second set of securing devices compresses the second conduit against the second end of the connector.

13. The vascular access system of claim 12, wherein the first and/or second connecting members comprise at least one ridge that spans at least a portion of an exterior circumference of the connector.

14. The vascular access system of claim 13, wherein the first set of securing devices and the second set of securing devices are configured to compress at least one of said conduits against said at least one ridge.

15. The vascular access system of claim 12, wherein the first and/or second conduits are configured with an impermeable wall segment in a portion nearest to the connector.

16. The vascular access system of claim 12, wherein the first and/or second conduits are configured with an elastomeric wall segment to reduce bleeding after puncture or to improve sealing of the connector.

17. The vascular access system of claim 12, further comprising a first therapeutic agent and a second therapeutic agent that are associated with one or both of an inner luminal surface and an outer abluminal surface of any of the first conduit, the second conduit, or the connector, wherein the vascular access system is configured to deliver a therapeutically effective dose of the first therapeutic agent and/or the second therapeutic agent to a mammal when the vascular access system is implanted within the mammal.

18. The vascular access system of claim 12, wherein the first connecting member or the second connecting member further comprises at least one of snap fits, interfits, teeth, threaded connectors, key system, tension clips, seals, friction ridges, or any combination thereof.

19. The vascular access system of claim 12, wherein the connector irreversibly couples to the first or the second conduit with the first connecting member or the second connecting member further comprising at least one of snap fits, interfits, teeth, threaded connectors, key system, tension clips, seals, friction ridges, or any combination thereof.

20. The vascular access system of claim 12, wherein the first conduit has different pliability than the second conduit.

21. The vascular access system of claim 12, wherein the inside luminal wall of the connector comprises ridges that spiral along a length of the connector that are configured to enhance laminar flow.

* * * * *